United States Patent
Miyaki et al.

(10) Patent No.: US 11,508,104 B2
(45) Date of Patent: Nov. 22, 2022

(54) MEDICAL IMAGE PROCESSING APPARATUS, MEDICAL IMAGE PROCESSING METHOD, AND STORAGE MEDIUM

(71) Applicant: CANON MEDICAL SYSTEMS CORPORATION, Otawara (JP)

(72) Inventors: Keisuke Miyaki, Utsunomiya (JP); Yu Igarashi, Utsunomiya (JP); Koichiro Kurita, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 139 days.

(21) Appl. No.: 16/872,430

(22) Filed: May 12, 2020

(65) Prior Publication Data

US 2020/0273227 A1    Aug. 27, 2020

Related U.S. Application Data

(63) Continuation of application No. PCT/JP2019/043391, filed on Nov. 6, 2019.

(30) Foreign Application Priority Data

Nov. 22, 2018  (JP) .............................. JP2018-218939

(51) Int. Cl.
*G06T 11/60* (2006.01)
*G06T 7/50* (2017.01)
(Continued)

(52) U.S. Cl.
CPC ............ *G06T 11/60* (2013.01); *A61B 8/0841* (2013.01); *A61B 8/0883* (2013.01); *A61B 8/461* (2013.01);
(Continued)

(58) Field of Classification Search
None
See application file for complete search history.

(56) References Cited

U.S. PATENT DOCUMENTS

| 2014/0303719 | A1* | 10/2014 | Cox ...................... A61F 2/2418 623/2.37 |
| 2015/0348263 | A1 | 12/2015 | Yamamori et al. |
| 2015/0370995 | A1 | 12/2015 | Wakai |

FOREIGN PATENT DOCUMENTS

| CN | 10-6845020 A | 6/2017 |
| JP | 2011-234863 A | 11/2011 |

(Continued)

OTHER PUBLICATIONS

International Search Report dated Jan. 7, 2020 in PCT/JP2019/043391 filed on Nov. 6, 2019, (with English Translation of Categories of Cited Documents), 3 pages.

(Continued)

*Primary Examiner* — Yanna Wu
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured to obtain a measurement value related to the shape of a heart valve in medical image data. The processing circuitry is configured to cause a display to display a numerical value related to the shape of an artificial valve to be placed for the heart valve.

15 Claims, 13 Drawing Sheets

(51) Int. Cl.
  *A61B 8/08* (2006.01)
  *A61B 8/00* (2006.01)
  *G06T 7/00* (2017.01)

(52) U.S. Cl.
  CPC .............. *G06T 7/0012* (2013.01); *G06T 7/50* (2017.01); *G06T 2207/10081* (2013.01); *G06T 2207/10088* (2013.01); *G06T 2207/10132* (2013.01); *G06T 2207/30048* (2013.01); *G06T 2207/30101* (2013.01); *G06T 2210/41* (2013.01)

(56) References Cited

FOREIGN PATENT DOCUMENTS

| JP | 2014-188323 | A | 10/2014 |
| JP | 2015-100618 | A | 6/2015 |
| JP | 2015-226693 | A | 12/2015 |
| JP | 2018-068640 | A | 5/2018 |
| KR | 10-1611475 | B1 | 4/2016 |

OTHER PUBLICATIONS

Office Action dated Sep. 27, 2022, in corresponding Japanese Patent Application No. 2018-218939.
Office Action dated Sep. 7, 2022, in Chinese Patent Application No. 2019800005709.1, citing document Nos. 15, 1-6, and 17

\* cited by examiner

MEDICAL IMAGE PROCESSING APPARATUS, MEDICAL IMAGE PROCESSING METHOD, AND STORAGE MEDIUM

CROSS-REFERENCE TO RELATED APPLICATIONS

This application is a continuation of International Application No. PCT/JP2019/043391, filed on Nov. 6, 2019 which claims the benefit of priority from Japanese Patent Application No. 2018-218939 filed on Nov. 22, 2018, the entire contents of which are incorporated herein by reference.

FIELD

Embodiments described herein relate generally to a medical image processing apparatus, a medical image processing method, and a storage medium.

BACKGROUND

Treatment methods conventionally known for valvular heart diseases include internal treatments realized with administration of drugs and surgical treatments realized with a valve replacement to attach a new artificial valve or a valve formation procedure to repair a part of a valve. Further, for surgical treatments in recent years, treatment methods using a catheter to reduce the burden on the subject have been established. For example, a typical treatment method for aortic valve stenosis is called Transcatheter Aortic Valve Implantation (TAVI) by which an artificial valve is placed on the valve annulus of the aortic valve by using a catheter. When implementing such a valve replacement, it is necessary to accurately learn the shapes of the valve annulus and the surrounding site, to determine the specification of the artificial valve to be placed.

DETAILED DESCRIPTION

Figure 1:
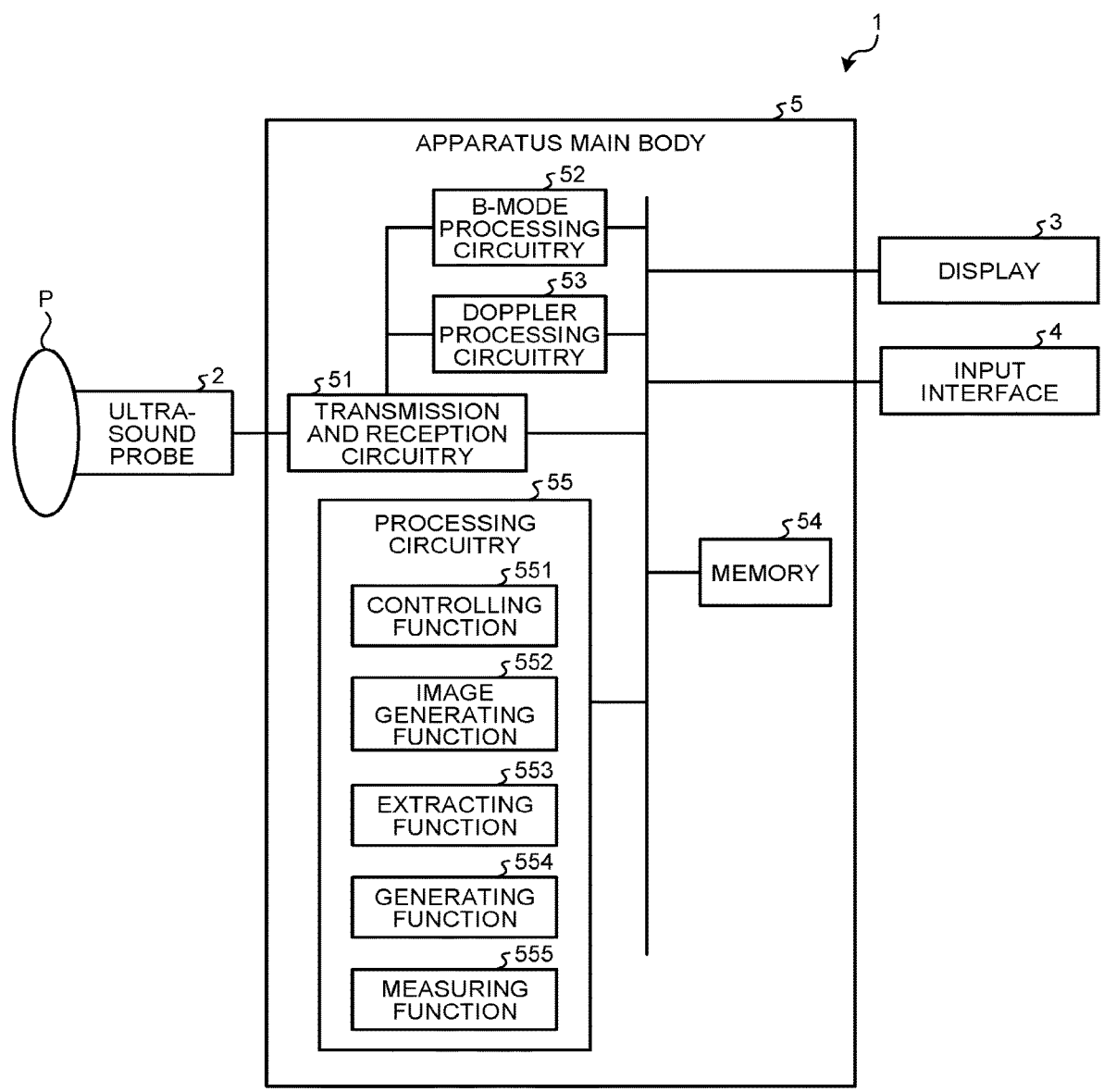
FIG. 1 is a block diagram illustrating an exemplary configuration of an ultrasound diagnosis apparatus according to a first embodiment.

A medical image processing apparatus according to an embodiment includes processing circuitry. The processing circuitry is configured to obtain a measurement value related to the shape of a heart valve in medical image data. The processing circuitry is configured to cause a display to display a numerical value related to the shape of an artificial valve to be placed for the heart valve.

Exemplary embodiments of a medical image processing apparatus, a medical image processing method, and a storage medium of the present disclosure will be explained in detail, with reference to the accompanying drawings. Possible embodiments of the medical image processing apparatus, the medical image processing method, and the storage medium of the present disclosure are not limited to those described below. Further, some of the constituent elements in the following description that are the same as one another will be referred to by using the same reference characters, and duplicate explanations will be omitted.

First Embodiment

To begin with, a medical image processing apparatus according to a first embodiment will be explained. In the present embodiment, an example will be explained in which a medical image processing apparatus of the present disclosure is included in an ultrasound diagnosis apparatus. FIG. 1 is a block diagram illustrating an exemplary configuration of an ultrasound diagnosis apparatus 1 according to the first embodiment. As illustrated in FIG. 1, the ultrasound diagnosis apparatus 1 according to the present embodiment includes an ultrasound probe 2, a display 3, an input interface 4, and an apparatus main body 5. The ultrasound probe 2, the display 3, and the input interface 4 are communicably connected to the apparatus main body 5.

The ultrasound probe 2 is connected to transmission and reception circuitry 51 included in the apparatus main body 5. For example, the ultrasound probe 2 includes a plurality of piezoelectric transducer elements in the probe main body. Each of the plurality of piezoelectric transducer elements is configured to generate an ultrasound wave on the basis of a drive signal supplied thereto from the transmission and reception circuitry 51. Further, the ultrasound probe 2 is configured to receive reflected waves from a subject P and to convert the received reflected waves into electric signals. Further, the ultrasound probe 2 includes, in the probe main body, a matching layer provided for the piezoelectric transducer elements, as well as a backing member or the like that prevents the ultrasound waves from propagating rearward from the piezoelectric transducer elements. The ultrasound probe 2 is detachably connected to the apparatus main body 5. For example, the ultrasound probe 2 may be an ultrasound probe of a sector type, a linear type, or a convex type.

When an ultrasound wave is transmitted from the ultrasound probe 2 to the subject P, the transmitted ultrasound wave is repeatedly reflected on a surface of discontinuity of acoustic impedances at a tissue in the body of the subject P and is received as a reflected-wave signal by each of the plurality of piezoelectric transducer elements included in the ultrasound probe 2. The amplitude of the received reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction.

The ultrasound probe 2 may be an ultrasound probe configured to mechanically swing the plurality of piezoelectric transducer elements included in a one-dimensional ultrasound probe in which the plurality of piezoelectric transducer elements are arranged in a row or may be an ultrasound probe realized as a two-dimensional ultrasound probe in which the plurality of piezoelectric transducer elements are two-dimensionally arranged in a matrix formation. The ultrasound probe 2 is capable of three-dimensionally scanning the subject P.

The display 3 is configured to display a Graphical User Interface (GUI) used by an operator of the ultrasound diagnosis apparatus 1 for inputting various types of setting requests through the input interface 4 and to display ultrasound images, display information, and the like generated in the apparatus main body 5. In this situation, the display information includes, for example, measurement values related to the shape of a heart valve in ultrasound image data, numerical values indicating the shape of an artificial valve to be placed for the heart valve, a shape estimation model indicating the shape of the heart valve, an artificial valve model indicating the shape of the artificial valve, and the like. These elements of the display information will be explained in detail later. Further, the display 3 is configured to display various types of messages and the display information to notify the operator of processing statuses and processing results of the apparatus main body 5. Further, the display 3 includes a speaker and is capable of also outputting audio.

The input interface 4 is configured to receive operations to set a prescribed position (e.g., a region of interest), to set a display orientation of an image, to input a numerical value, and the like. For example, the input interface 4 may be realized by using a trackball, a switch button, a mouse, a keyboard, a touchpad on which an input operation is performed by touching the operation surface thereof, a touch monitor in which a display screen and a touchpad are integrally formed, a contactless input circuit using an optical sensor, an audio input circuit and/or the like. The input interface 4 is connected to processing circuitry 55 (explained later) and is configured to convert input operations received from the operator into electric signals and to output the electric signals to the processing circuitry 55. In the present disclosure, the input interface 4 does not necessarily have to include one or more physical operation component parts such as a mouse and a keyboard. For instance, possible examples of the input interface include an electric signal processing circuit configured to receive an electric signal corresponding to an input operation from an external input device provided separately from the apparatus and to output the electric signal to the processing circuitry 55.

The apparatus main body 5 includes the transmission and reception circuitry 51, B-mode processing circuitry 52, Doppler processing circuitry 53, a memory 54, and the processing circuitry 55. In the ultrasound diagnosis apparatus 1 illustrated in FIG. 1, the processing functions are stored in the memory 54 in the form of computer-executable programs. The transmission and reception circuitry 51, the B-mode processing circuitry 52, the Doppler processing circuitry 53, and the processing circuitry 55 are processors configured to realize the functions corresponding to the programs, by reading and executing the programs from the memory 54. In other words, the circuits that have read the programs have the functions corresponding to the read programs.

The transmission and reception circuitry 51 includes a pulse generator, a transmission delay circuit, a pulser, and the like and is configured to supply the drive signal to the ultrasound probe 2. The pulse generator is configured to repeatedly generate a rate pulse used for forming transmission ultrasound wave at a predetermined rate frequency. Further, the transmission delay circuit is configured to apply a delay time period that is required to converge the ultrasound waves generated from the ultrasound probe 2 into the form of a beam and to determine transmission directionality and that corresponds to each of the piezoelectric transducer elements, to each of the rate pulses generated by the pulse generator. Further, the pulser is configured to apply the drive signal (a drive pulse) to the ultrasound probe 2 with timing based on the rate pulses. In other words, by varying the delay time periods applied to the rate pulses, the transmission delay circuit arbitrarily adjusts the transmission directions of the ultrasound waves transmitted from the surfaces of the piezoelectric transducer elements.

The transmission and reception circuitry 51 has a function that is able to instantly change the transmission frequency, the transmission drive voltage, and the like, for the purpose of executing a predetermined scan sequence on the basis of an instruction from the processing circuitry 55 (explained later). In particular, the function to change the transmission drive voltage is realized by using a linear-amplifier-type transmission circuit of which the value can be instantly switched or by using a mechanism configured to electrically switch between a plurality of power source units.

Further, the transmission and reception circuitry 51 includes a pre-amplifier, an Analog/Digital (A/D) converter, a reception delay circuit, an adder, and the like and is configured to generate reflected-wave data by performing various types of processes on the reflected-wave signals received by the ultrasound probe 2. The pre-amplifier is configured to amplify the reflected-wave signal for each of the channels. The A/D converter is configured to perform an A/D conversion on the amplified reflected-wave signals. The reception delay circuit is configured to apply a delay time period required to determine reception directionality. The adder is configured to generate the reflected-wave data by performing an adding process on the reflected-wave signals processed by the reception delay circuit. As a result of the adding process performed by the adder, reflected components of the reflected-wave signals that are from the direction corresponding to the reception directionality are emphasized, so that a comprehensive beam used in the ultrasound wave transmission and reception is formed on the basis of the reception directionality and the transmission directionality.

The B-mode processing circuitry 52 is configured to generate data (B-mode data) in which the signal intensity is expressed by a degree of brightness, by receiving the reflected-wave data from the transmission and reception circuitry 51 and performing a logarithmic amplification, an envelope detecting process, or the like thereon.

The Doppler processing circuitry 53 is configured to generate data (Doppler data) obtained by extracting moving member information such as velocity, dispersion, power, and the like with respect to multiple points, by performing a frequency analysis to obtain velocity information from the reflected-wave data received from the transmission and reception circuitry 51 and extracting a blood flow, a tissue, and a contrast agent echo component subject to the Doppler effect. The moving members in the present embodiment are fluids such as blood flowing in blood vessels, lymph flowing in lymphatic ducts, and/or the like.

The B-mode processing circuitry 52 and the Doppler processing circuitry 53 are each capable of processing both two-dimensional reflected-wave data and three-dimensional reflected-wave data. In other words, the B-mode processing circuitry 52 is configured to generate two-dimensional B-mode data from two-dimensional reflected-wave data and to generate three-dimensional B-mode data from three-dimensional reflected-wave data. Further, the Doppler processing circuitry 53 is configured to generate two-dimensional Doppler data from two-dimensional reflected-wave data and to generate three-dimensional Doppler data from three-dimensional reflected-wave data. The three-dimensional B-mode data is data in which a brightness value is assigned in correspondence with the intensity of reflection from a reflection source positioned at each of a plurality of points (sampling points) set on scanning lines within a three-dimensional scanned range. Further, the three-dimensional Doppler data is data in which a brightness value is assigned in correspondence with a value of blood flow information (velocity, dispersion, and power) to each of a plurality of points (sampling points) set on the scanning lines within the three-dimensional scanned range.

The memory 54 is configured to store therein display-purpose image data generated by the processing circuitry 55. Further, the memory 54 is also capable of storing therein any of the data generated by the B-mode processing circuitry 52 and the Doppler processing circuitry 53. Further, the memory 54 is also configured to store therein control programs for performing ultrasound wave transmissions and receptions, image processing processes, and display processes, as well as various types of data such as diagnosis information (e.g., patients' IDs, medical doctors' observations), diagnosis protocols, various types of body marks, and the like. Further, the memory 54 is also configured to store therein the display information (measurement values related to the shape of a heart valve in image data, numerical values indicating the shape of an artificial valve to be placed for the heart valve, a shape estimation model indicating the shape of the heart valve, an artificial valve model indicating the shape of the artificial valve, and the like). The display information will be explained in detail later.

The processing circuitry 55 is configured to control the entirety of processes performed by the ultrasound diagnosis apparatus 1. More specifically, the processing circuitry 55 performs various types of processes by reading and executing programs corresponding to a controlling function 551, an image generating function 552, an extracting function 553, a generating function 554, and a measuring function 555 illustrated in FIG. 1, from the memory 54. In this situation, the controlling function 551 is an example of the controlling unit. The generating function 554 is an example of the generating unit. The measuring function 555 is an example of the obtaining unit.

The controlling function 551 is configured to control processes performed by the transmission and reception circuitry 51, the B-mode processing circuitry 52, and the Doppler processing circuitry 53, on the basis of the various types of setting requests input from the operator via the input interface 4, as well as various types of control programs and various types of data read from the memory 54. Further, the controlling function 551 is configured to exercise control so that the display 3 displays the display-purpose ultrasound image data stored in the memory 54. Further, the controlling function 551 is configured to exercise control so that the display 3 displays processing results obtained by the functions. For example, the controlling function 551 exercises control so that the display 3 displays the display information.

The image generating function 552 is configured to generate the ultrasound image data from the data generated by the B-mode processing circuitry 52 and the Doppler processing circuitry 53. In other words, the image generating function 552 is configured to generate B-mode image data in which the intensities of the reflected waves are expressed as brightness levels, from the two-dimensional B-mode data generated by the B-mode processing circuitry 52. The B-mode image data is data rendering the shape of a tissue in the region subject to an ultrasound scan. Further, the image generating function 552 is configured to generate Doppler image data indicating the moving member information, from the two-dimensional Doppler data generated by the Doppler processing circuitry 53. The Doppler image data is velocity image data, dispersion image data, power image data, or image data combining together any of these types of image data. The Doppler image data is data indicating fluid information related to the fluid flowing through the region subject to an ultrasound scan.

In this situation, generally speaking, the image generating function 552 converts (by performing a scan convert process) a scanning line signal sequence from an ultrasound scan into a scanning line signal sequence in a video format used by, for example, television and generates the display-purpose ultrasound image data. More specifically, the image generating function 552 generates the display-purpose ultrasound image data by performing a coordinate transformation process compliant with the ultrasound scanning mode used by the ultrasound probe 2. Further, as various types of image processing processes besides the scan convert process, the image generating function 552 performs, for example, an image processing process (a smoothing process) to re-generate an average brightness value image, an image processing process (an edge enhancement process) that uses a differential filter inside an image, or the like, by using a plurality of image frames resulting from the scan convert process. Also, the image generating function 552 combines text information of various types of parameters, scale graduations, body marks, and the like with the ultrasound image data.

In other words, the B-mode data and the Doppler data are each ultrasound image data before the scan convert process. The data generated by the image generating function 552 is the display-purpose ultrasound image data after the scan convert process. The B-mode data and the Doppler data may be referred to as raw data.

Further, the image generating function 552 is configured to generate three-dimensional B-mode image data by performing a coordinate transformation process on the three-dimensional B-mode data generated by the B-mode processing circuitry 52. Further, the image generating function 552 is configured to generate three-dimensional Doppler image data by performing a coordinate transformation process on the three-dimensional Doppler data generated by the Doppler processing circuitry 53. The three-dimensional B-mode data and the three-dimensional Doppler data are each volume data before the scan convert process. In other words, the image generating function 552 generates "the three-dimensional B-mode image data and the three-dimensional Doppler image data" as "volume data represented by three-dimensional ultrasound image data".

Further, the image generating function 552 is also capable of performing a rendering process on the volume data, for the purpose of generating various types of two-dimensional image data used for displaying the volume data on the display 3. The extracting function 553 is configured to extract the heart valve in the ultrasound image data. The generating function 554 is configured to generate the shape estimation model indicating the shape of the heart valve extracted by the extracting function 553. The measuring function 555 is configured to measure measurement values related to the shape of the heart valve extracted by the extracting function 553. Processes performed by the extracting function 553, the generating function 554, and the measuring function 555 will be explained in detail later.

An overall configuration of the ultrasound diagnosis apparatus 1 according to the first embodiment has thus been explained. The ultrasound diagnosis apparatus 1 according to the first embodiment structured as described above makes it possible to facilitate the process of determining the specification of an artificial valve to be placed. More specifically, the ultrasound diagnosis apparatus 1 according to the first embodiment makes it possible to facilitate the process of determining the specification of the artificial valve to be placed, by presenting a comparative display of the measurement values related to the shape of the heart valve extracted from medical image data, with numerical values indicating the shape of the artificial valve to be placed for the heart valve.

As explained above, when performing a valve replacement, the specification of an artificial valve to be placed is determined after accurately understanding the shapes of the valve annulus and the surrounding site thereof. In this situation, because artificial valves are available in various specifications, it may be difficult in some situations to select an appropriate specification from among the various options. Further, the selected specification may vary depending on the medical doctor's experience. It is therefore not easy to properly determine the specification of the artificial valve to be placed. To cope with this situation, the ultrasound diagnosis apparatus 1 according to the first embodiment makes it easier to judge whether or not the specification of an artificial valve to be placed is appropriate by presenting a comparative display of the measurement values related to the shape of the heart valve with the numerical values indicating the shape of the artificial valve and thus makes it possible to facilitate the process of determining the specification of the artificial valve to be placed.

Next, details of the ultrasound diagnosis apparatus 1 according to the first embodiment will be explained. The extracting function 553 is configured to extract a heart valve in medical image data. More specifically, the extracting function 553 extracts a surrounding region including the heart valve, from the medical image data acquired of the heart. For example, the extracting function 553 extracts the surrounding region including the heart valve in three-dimensional ultrasound image data acquired of the heart.

Figure 2:
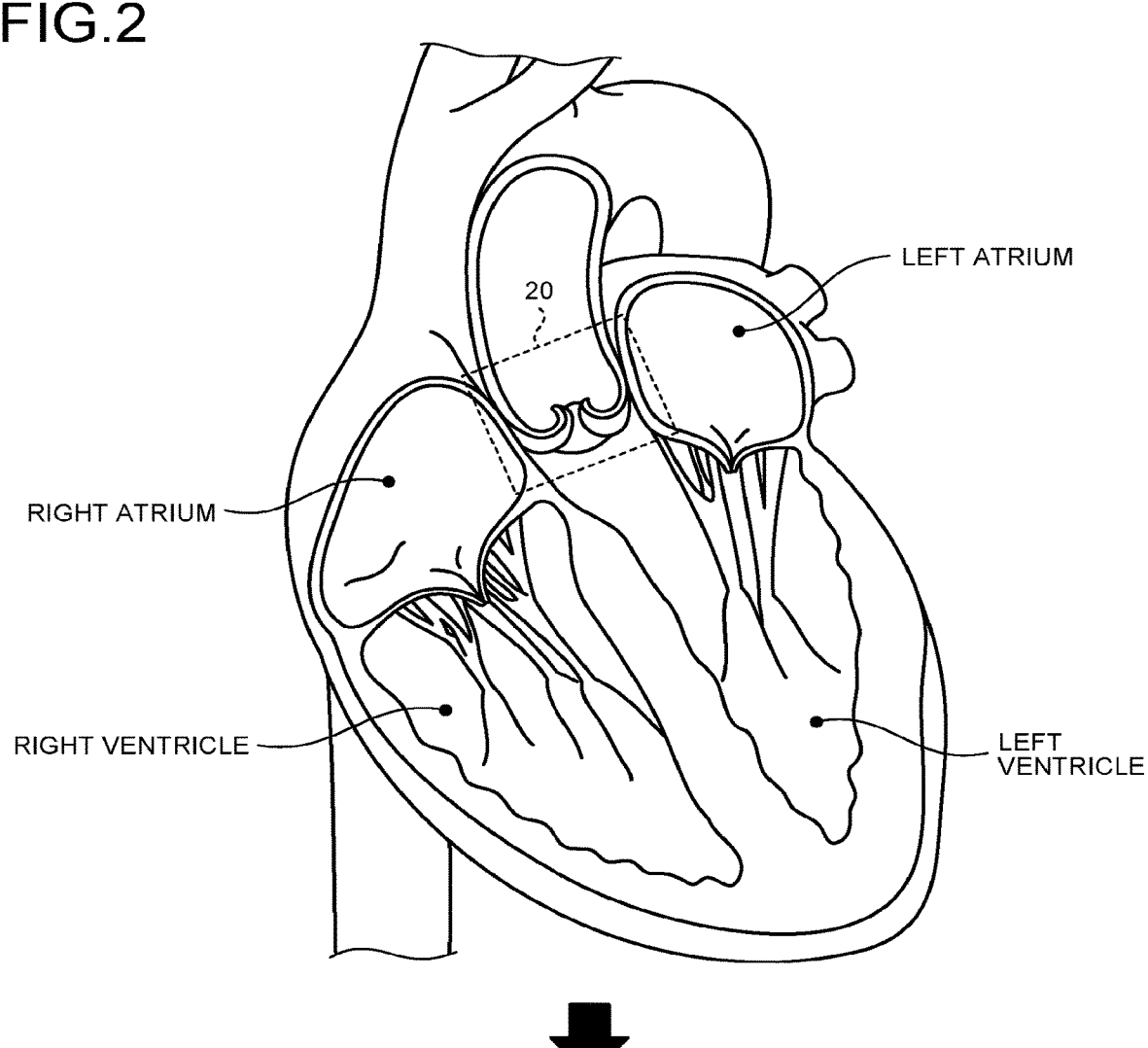
FIG. 2 is a drawing for explaining an example of an extracting process performed by an extracting function according to the first embodiment.
Figure 2:
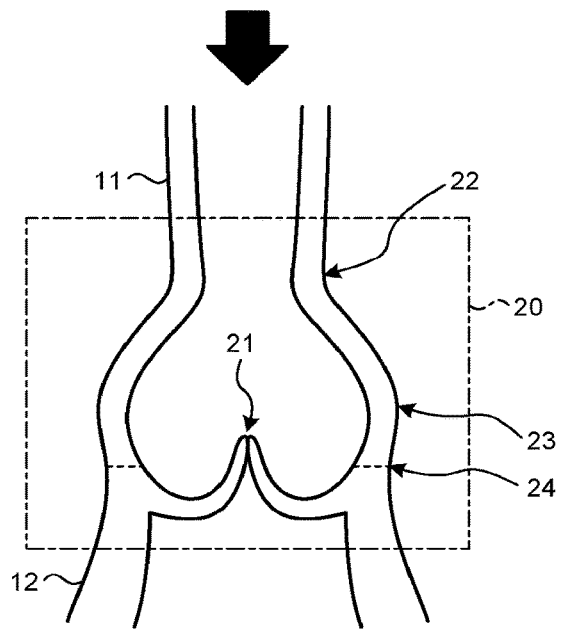

FIG. 2 is a drawing for explaining an example of the extracting process performed by the extracting function 553 according to the first embodiment. FIG. 2 illustrates an example in which a surrounding region including the aortic valve is to be extracted. In FIG. 2, the top section illustrates the entire heart, while the bottom section illustrates the surroundings of the aortic valve. In the following explanations, the surrounding region including the aortic valve extracted by the extracting function 553 will be referred to as an "aortic valve composite".

For example, as illustrated in the top section of FIG. 2, the extracting function 553 extracts a region corresponding to the left ventricle and a region corresponding to the ascending aorta and extracts a region including the boundaries of the extracted regions as an aortic valve composite 20. In this situation, the extracting function 553 extracts regions corresponding to the left ventricle, the right ventricle, the left atrium, the right atrium, the ascending aorta, and the pulmonary artery from the three-dimensional ultrasound image data related to the heart by using a publicly-known image processing technique, and further, extracts the boundaries of the regions. In this situation, for example, the extracting function 553 extracts the regions on the basis of front-and-back directions, left-and-right directions, and up-and-down directions defined in the three-dimensional ultrasound image data, as well as an anatomical positional relationship among the left ventricle, the right ventricle, the left atrium, and the right atrium of the heart, the ascending aorta, and the pulmonary artery.

For example, the aortic valve composite 20 extracted by the extracting function 553 includes, as illustrated in the bottom section of FIG. 2, the valve annulus 21, the Sinotubular (ST) Junction 22, the sinus of Valsalva 23, and an annulus (which may also be referred to as the anatomical ventriculo-arterial junction) 24 that are positioned between the ascending aorta 11 and the left ventricle 12. In this situation, the sinus of Valsalva 23 is a bulging part at the starting section of the ascending aorta 11. The ST junction 22 is a part where the ascending aorta 11 and the sinus of Valsalva 23 join with each other. The annulus 24 is a part where the left ventricle 12 and the sinus of Valsalva 23 join with each other.

Although FIG. 2 illustrates the example in which the aortic valve composite is extracted, the extracting function 553 is also capable of extracting any of the other heart valves in the same manner as described above. For example, the extracting function 553 is capable of extracting a region corresponding to the left ventricle and a region corresponding to the left atrium and extracting a region including the boundaries of the extracted regions as a mitral valve composite. As another example, the extracting function 553 is also capable of extracting a region corresponding to the right ventricle and a region corresponding to the right atrium and extracting a region including the boundaries of the extracted regions as a tricuspid valve composite. As yet another example, the extracting function 553 is also capable of extracting a region corresponding to the right ventricle and a region corresponding to the pulmonary artery and extracting a region including the boundaries of the extracted regions as a pulmonary artery composite.

The extracting method described above is merely an example. The extracting function 553 is capable of extracting the aortic valve composite and the like by using other existing extracting methods.

The generating function 554 is configured to generate a heart valve model indicating the shape of the heart valve extracted by the extracting function 553. More specifically, the generating function 554 is configured to generate a shape estimation model indicating the shape of the surrounding region including the heart valve extracted by the extracting function 553. For example, the extracting function 553 generates a shape estimation model of the aortic valve composite 20 extracted from the three-dimensional ultrasound image data by the extracting function 553.

In one example, the generating function 554 generates a three-dimensional shape estimation model indicating a three-dimensional structure of a contour line of the inner wall and a contour line of the outer wall of the aortic valve composite 20 extracted by the extracting function 553. Alternatively, the shape estimation model may be generated by using a standard model of a surrounding region including the heart valve. In that situation, for example, the memory 54 has the standard model stored therein, so that the generating function 554 generates the shape estimation model, by reading the standard model corresponding to the heart valve for which a model is to be generated and re-shaping the standard model on the basis of the extraction result of the surrounding region. For example, the generating function 554 generates the shape estimation model of the aortic valve composite by reading a standard model of an aortic valve composite from the memory 54 and re-shaping the standard model on the basis of the shape of the aortic valve composite 20.

The process of generating the shape estimation model described above is merely an example. It is possible to generate the shape estimation model of the aortic valve composite and the like by using other existing generating methods.

The measuring function 555 is configured to obtains the measurement values related to the shape of the heart valve in the medical image data. More specifically, the measuring function 555 measures the measurement values related to the shape of the extracted heart valve. Even more specifically, the measuring function 555 measures the measurement values related to the shape of a heart valve model. For example, the measuring function 555 measures various types of parameters indicating the shape with respect to the shape estimation model of the aortic valve composite 20 generated by the generating function 554.

Figure 3:
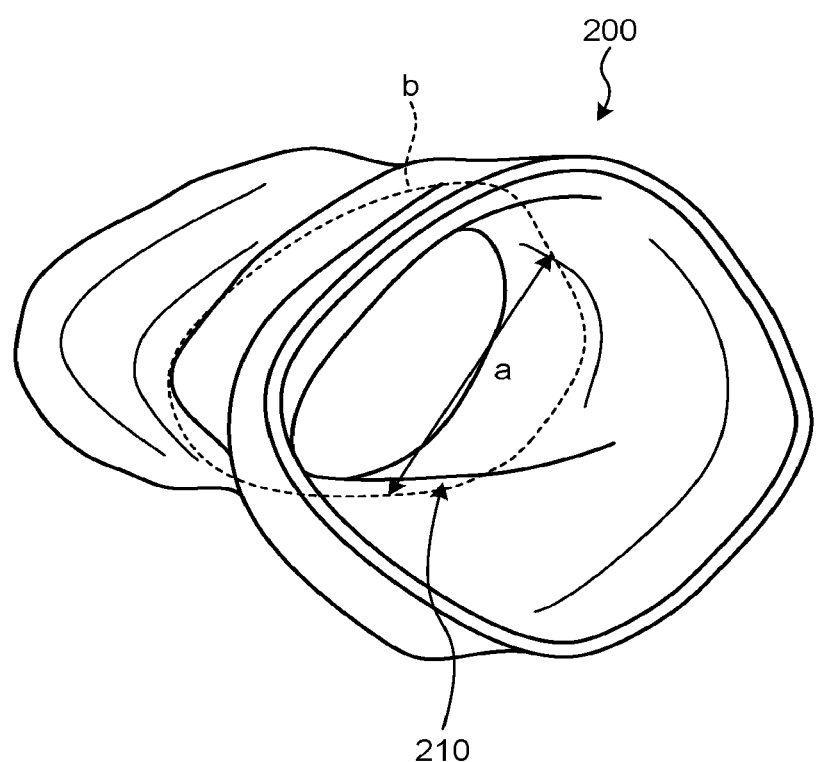
FIG. 3 is a drawing for explaining an example of a measuring process performed by a measuring function according to the first embodiment.

FIG. 3 is a drawing for explaining an example of the measuring process performed by the measuring function 555 according to the first embodiment. In this situation, FIG. 3 illustrates a process of measuring parameters of a shape estimation model 200 of the aortic valve composite 20 generated by the generating function 554. For example, as illustrated in FIG. 3, the measuring function 555 measures the diameter "a" and the perimeter "b" of the valve annulus 210 in the shape estimation model 200. In this situation, the measuring function 555 is capable of measuring the maximum diameter and the minimum diameter of the valve annulus, as the diameter of the valve annulus 210.

Further, as for the parameters to be measured, the measuring function 555 is capable of measuring various types of parameters of the shape estimation model 200 such as the height of the valve annulus 210, the diameter and the perimeter of the ascending aorta, and the diameter and the perimeter of the sinus of Valsalva, besides the diameter "a" and the perimeter "b" of the valve annulus 210. For example, the parameters to be measured may arbitrarily be selected by the operator or may be modified by the operator from certain parameters determined by default.

Figure 4A:
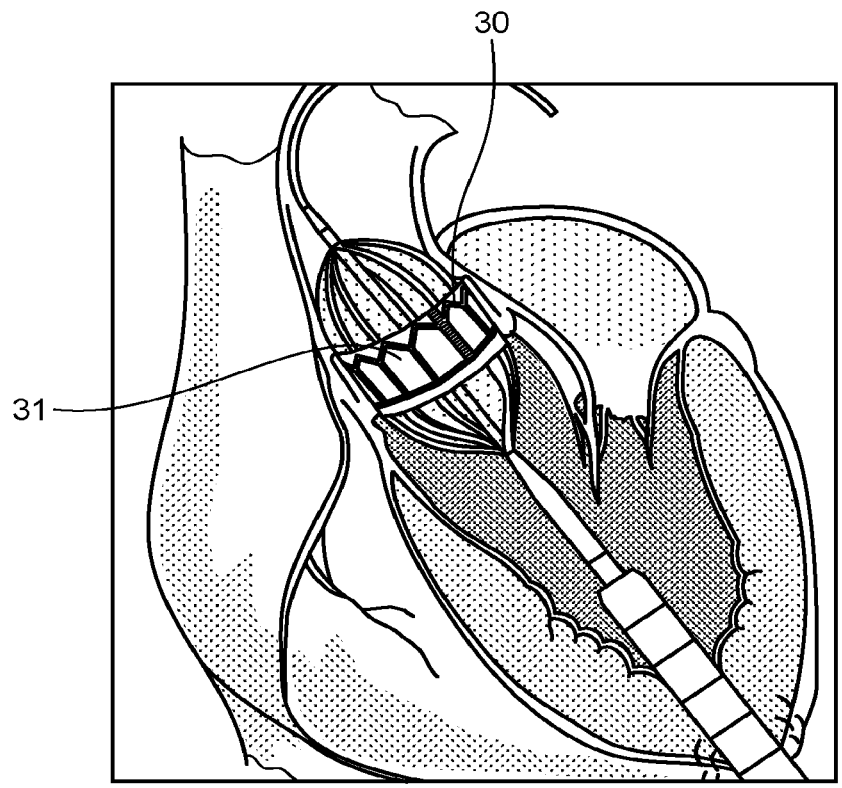
FIG. 4A is a drawing illustrating an example of a placement of an artificial valve according to the first embodiment.

When the measuring function 555 has measured the measurement values related to the shape of the heart valve, the controlling function 551 is configured to present a comparative display of the measurement values with numerical values related to the shape of an artificial valve to be placed for the heart valve. As explained above, for the artificial valve, an appropriate specification is selected from among various specifications. For example, as illustrated in FIG. 4A, the artificial valve is placed on the valve annulus by using a catheter. FIG. 4A is a drawing illustrating an example of the placement of the artificial valve according to the first embodiment. Although FIG. 4A illustrates placing an artificial valve 30 while using a transapical approach to the aortic valve, other examples of approaches to the aortic valve include a transfemoral approach, a trans-subclavian approach, and a transaortic approach.

Figure 4B:
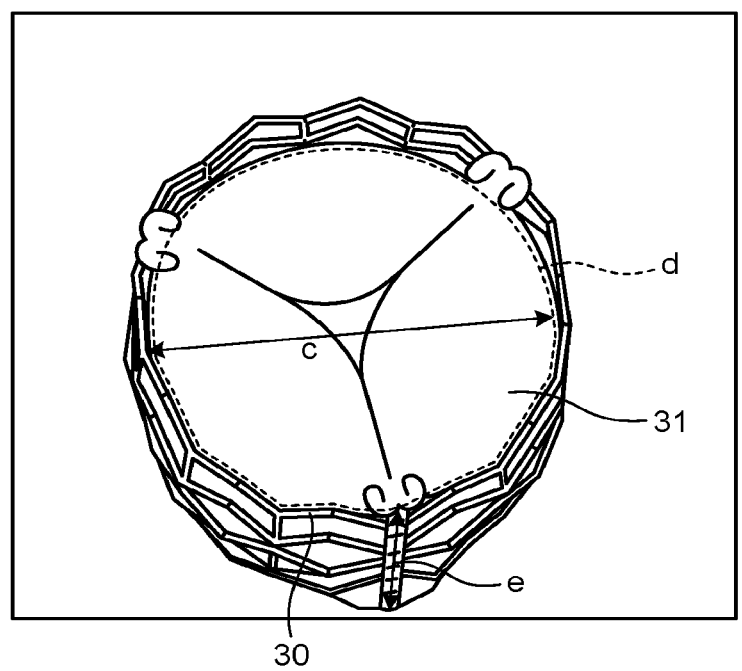
FIG. 4B is a drawing for explaining examples of parameters indicating the shape of the artificial valve according to the first embodiment.

For example, the artificial valve 30 to be placed for the aortic valve is formed by attaching a valve 31 to a stent, as illustrated in FIG. 4A. In this situation, for example, the parameters indicating the shape of the artificial valve 30 to be placed for the aortic valve include, as illustrated in FIG. 4B, the diameter "c", the perimeter "d", and the height "e" of the valve 31 of the artificial valve 30. FIG. 4B is a drawing for explaining the examples of the parameters indicating the shape of the artificial valve 30 according to the first embodiment.

In this situation, various types of parameters indicating shapes of artificial valves are stored in the memory 54 while being kept in correspondence with various specifications of the artificial valves. In other words, the memory 54 has stored therein the diameter, the perimeter, and the height of each of the valves in correspondence with the various specifications of the artificial valves. The parameters indicating the shapes of the artificial valves are not limited to the examples described above. For the shapes of the artificial valves, it is acceptable to store any other arbitrary pieces of information in correspondence with one another. Further, the artificial valve does not necessarily have to be attached to a stent as illustrated in FIGS. 4A and 4B. Stentless artificial valves are similarly applicable. Further, the valve of the artificial valve may be a biological valve or may be a mechanical valve.

Further, as for the various types of parameters indicating the shapes of the artificial valves, numerical values may be stored in the memory 54. Alternatively, artificial valve models indicating the shapes of the artificial valves with various specifications may be stored in the memory 54, so that the various types of parameters are obtained as a result of the measuring function 555 measuring the parameters indicating the shapes of the artificial valve models. The memory 54 is also capable of storing therein, for each of the various specifications, parameters indicating the shape of an artificial valve and an artificial valve model so as to be kept in correspondence with one another other.

The controlling function 551 is configured to display the various types of parameters indicating the shape of the artificial valve 30, together with the measurement values of the shape estimation model. In other words, the controlling function 551 causes the display 3 to display the measurement values measured by the measuring function 555, together with the parameters indicating the shape of the artificial valve. In this situation, as the parameters indicating the shape of the artificial valve, the controlling function 551 displays one selected from between: numerical values indicating the shape of an artificial valve designated by the operator; and conditions of the shape of an artificial valve applicable to the heart valve.

Figure 5A:
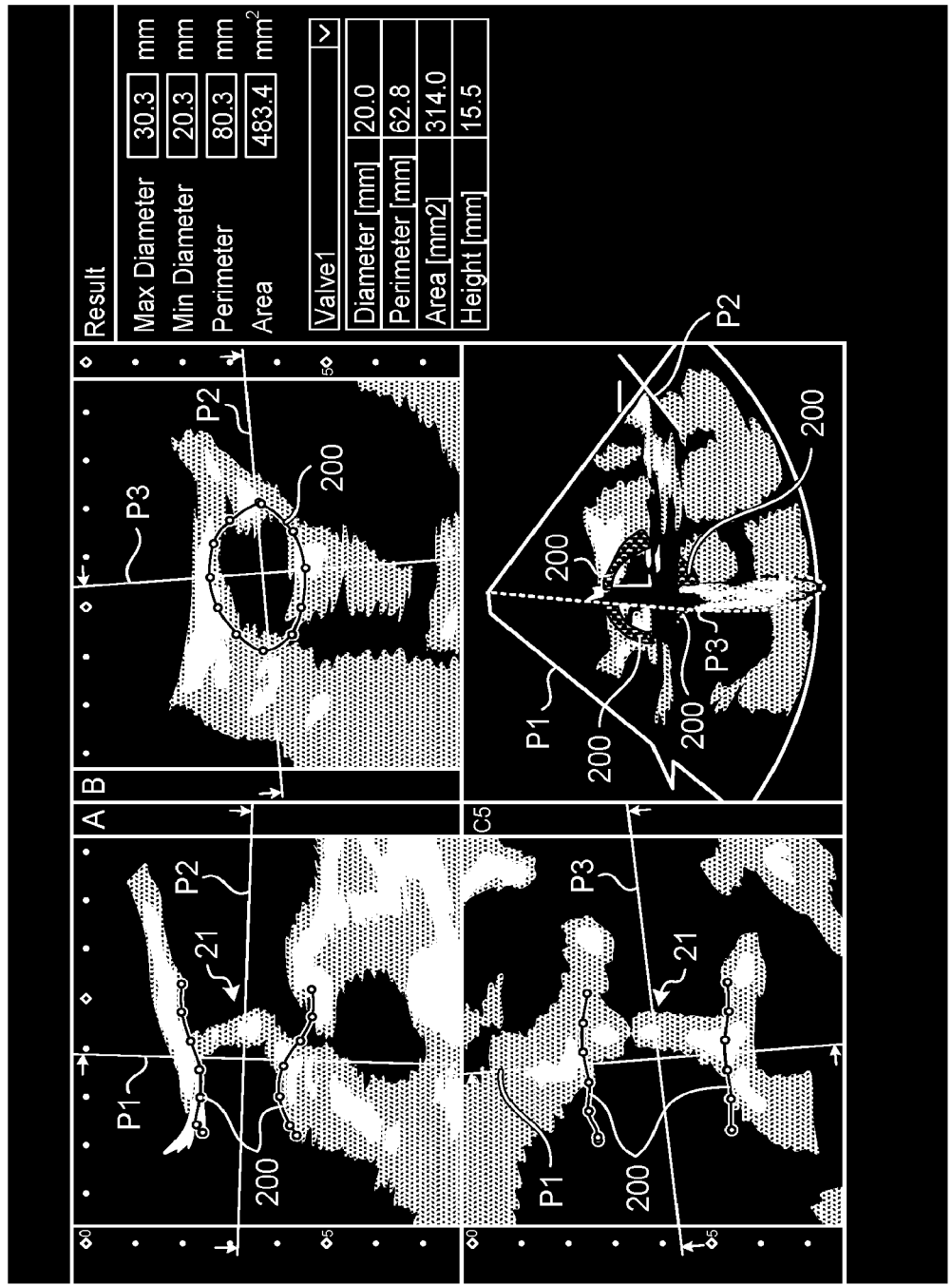
FIG. 5A is a drawing illustrating an example of display realized by a controlling function according to the first embodiment.
Figure 5B:
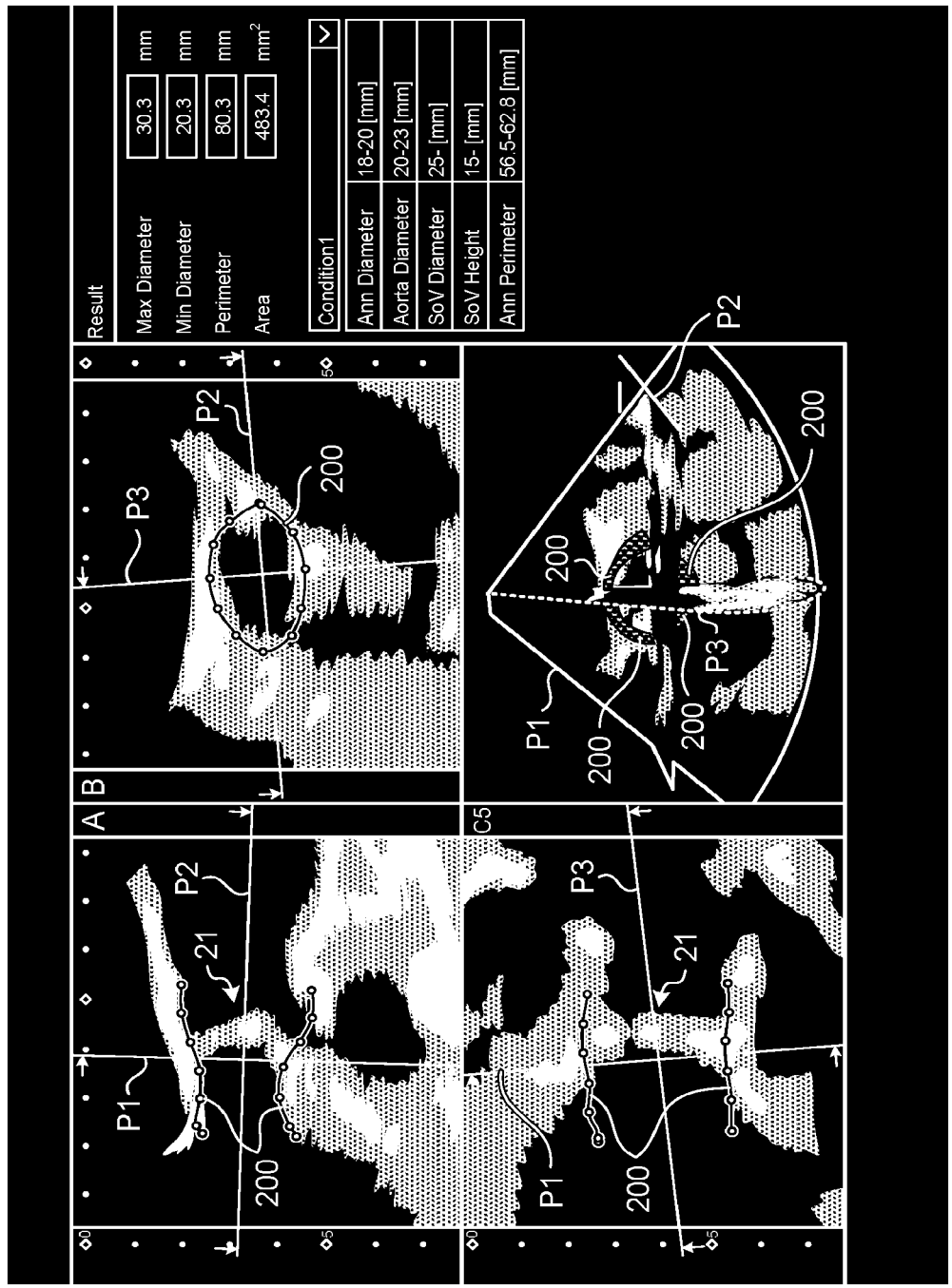
FIG. 5B is a drawing illustrating another example of the display realized by the controlling function according to the first embodiment.

Next, examples of the display of the parameters indicating the shape of the artificial valve will be explained, with reference to FIGS. 5A and 5B. FIGS. 5A and 5B are drawings illustrating examples of the display realized by the controlling function 551 according to the first embodiment. FIG. 5A illustrates an example in which, as the parameters indicating the shape of the artificial valve, numerical values indicating the shape of an artificial valve designated by the operator are displayed. In contrast, FIG. 5B illustrates an example in which, as the parameters indicating the shape of the artificial valve, conditions of the shape of an artificial valve applicable to the heart valve are displayed.

For example, as illustrated in FIG. 5A, the controlling function 551 causes the display 3 to display: ultrasound images (two images at the top and one image at the bottom left) on arbitrary three cross-sectional planes taken of the valve annulus 21; a three-dimensional ultrasound image (one image at the bottom right) in which the images on the three cross-sectional planes are three-dimensionally arranged; the measurement values of the shape estimation model ("Result" on the right side of the drawing); and the numerical values indicating the shape of the artificial valve. For example, the controlling function 551 obtains, from the image generating function 552, the images generated from the three-dimensional ultrasound image data from which the aortic valve composite 20 was extracted. The controlling function 551 also obtains the measurement result from the measuring function 555 and obtains the numerical values indicating the shape of the artificial valve from the memory 54. The controlling function 551 thus causes the display 3 to display these pieces of information simultaneously.

In this situation, the controlling function 551 obtains the numerical values indicating the shape of the artificial valve designated by the operator from the memory 54. For example, by manipulating the images illustrated in FIG. 5A, the operator is able to cause measurement values in desired positions to be displayed and is able to cause the numerical values of the specification of an artificial valve selected on the basis of the displayed measurement values to be displayed.

The cross-sectional image at the top left of FIG. 5A indicates a cross-section of the aortic valve composite 20 taken on a plane P3 orthogonal to a plane P1 and a plane P2. Further, the cross-sectional image at the bottom left of FIG. 5A indicates a cross-section of the aortic valve composite 20 taken on the plane P2 orthogonal to the plane P1 and the plane P3. Also, the cross-sectional image at the top right of FIG. 5A indicates a cross-section of the aortic valve composite 20 taken on the plane P1 orthogonal to the plane P2 and the plane P3. In addition, the cross-sectional image at the bottom right of FIG. 5A indicates an image in which the cross-sectional images taken on the planes P1, P2, and P3 are three-dimensionally arranged. Although the planes P1, P2, and P3 are orthogonal to one another in the present example in FIG. 5A, all the planes do not necessarily have to be orthogonal to one another. For example, the operator is able to have the measurement values measured in the position where the artificial valve is to be placed, by manipulating straight lines P1 to P3 defining the cross-sectional planes indicated in the two-dimensional images, and also, the positions, the orientations, and the like of the cross-sectional planes indicated in the image in which the two-dimensional images are three-dimensionally arranged.

In one example, by operating the input interface 4, the operator determines the positions of a diameter and a perimeter of the valve annulus 21 to be measured by the measuring function 555, by changing the position in the left-and-right direction and the inclination of the straight line P1 drawn in the image at the top left of FIG. 5A. Further, for example, by operating the input interface 4, the operator determines the position of a maximum diameter of the valve annulus 21 to be measured by the measuring function 555 by changing the position in the up-and-down direction and the inclination of the straight line P2 drawn in the image at the top right of FIG. 5A. Also, the operator determines the position of a minimum diameter of the valve annulus 21 to be measured by the measuring function 555 by changing the position in the left-and-right direction and the inclination of the straight line P3 drawn in the image at the top right of FIG. 5A.

As described above, the measurement positions of the maximum diameter and the minimum diameter may arbitrarily be designated by the operator. Alternatively, the measurement positions may automatically be determined by applying an ellipse approximation to the shape estimation model 200 displayed in the image at the top right of FIG. 5A. In that situation, the measuring function 555 determines an ellipse of the shape estimation model 200 approximating to the ellipse of the valve annuls, by causing the ellipse of the shape estimation model 200 to approximate to the cross-sectional plane of the valve annulus drawn as an elliptical shape in the image at the top right of FIG. 5A. Further, the measuring function 555 measures the diameters of the determined ellipses and further determines a diameter exhibiting a maximum value as the position of the maximum diameter and determines a diameter exhibiting a minimum value as the position of the minimum diameter. When the measurement position is automatically determined, the controlling function 551 is able to display the positions of the straight lines P1 to P3 defining the cross-sectional planes and the like, so as to vary by following the determined positions.

In this situation, as illustrated in FIG. 5A, the controlling function 551 is capable of causing the shape estimation model 200 to be displayed so as to be superimposed over each of the images, in a corresponding position within the image. As a result, the operator is able to have a measurement value measured in a desired position, while viewing the ultrasound images of the aortic valve composite 20 and the shape estimation model 200 at the same time. Further, the controlling function 551 is capable of receiving a correction to be made to the shape of the displayed shape estimation model 200. In other words, by operating the input interface 4, the operator is able to correct the shape estimation model 200 indicated in any of the images illustrated in FIG. 5A. For example, by referring to the shape of the aortic valve composite 20 indicated in any one of the ultrasound images on which the shape estimation model 200 is superimposed, the operator is able to correct the shape of the shape estimation model 200 generated by the generating function 554. With this configuration, it is possible to have the measurement values measured with a higher level of precision.

As explained above, when the operator has determined the positions in which the various types of parameters related to the shape of the shape estimation model 200 are to be measured, the measuring function 555 measures measurement values in the determined positions. For example, as illustrated in FIG. 5A, in the position corresponding to the valve annulus 21 in the shape estimation model 200, the measuring function 555 calculates "the maximum diameter ("Max Diameter"): 30.3 mm", "the minimum diameter ("Min Diameter"): 20.3 mm", "the perimeter: 80.3 mm", and "the area: 483.4 mm$^2$". The controlling function 551 causes the display 3 to display the calculated parameters.

Further, it is also possible to cause the measuring function 555 to perform the measuring process and the controlling function 551 to perform the display process, so as to follow changes made to positions by the operator. In other words, the measuring function 555 is capable of sequentially measuring parameters in various positions, by following the operations performed by the operator through the input interface 4. Further, the controlling function 551 is capable of causing the sequentially-measured parameters to be displayed, so as to sequentially change along with movements of the straight lines P1 to P3 defining the cross-sectional planes.

When having performed the measuring process that uses the shape estimation model 200 as described above, the operator refers to the measured parameters and selects a specification of the artificial valve to be placed on the valve annulus 21. For example, from a pull-down menu illustrated in FIG. 5A used for selecting an artificial valve, the operator selects an artificial valve "Valve 1". The controlling function 551 reads the numerical values stored in correspondence with the selected artificial valve "Valve 1" and causes the display 3 to display the read numerical values. For example, the controlling function 551 reads "the diameter: 20.0 mm", "the perimeter: 62.8 mm", "the area: 314.0 mm$^2$", and "the height: 15.5 mm" of the artificial valve "Valve 1" from the memory 54 and presents a comparative display of the read numerical values with the measurement values.

With this configuration, the operator is able to easily judge whether or not the artificial valve having the specification he/she selected is appropriate and is thus able to easily determine the specification of the artificial valve to be placed. As for the numerical values related to the shape of the artificial valve, it is also acceptable to read an artificial valve model from the memory 54 and to measure the corresponding parameters.

Further, for example, as illustrated in FIG. 5B, as the parameters indicating the shape of an artificial valve, the controlling function 551 is also capable of displaying conditions of the shape of an artificial valve applicable to the heart valve. In one example, similarly to the example explained with reference to FIG. 5A, when the operator has determined the positions in which the various parameters related to the shape of the shape estimation model 200 are to be measured, the measuring function 555 measures measurement values in the determined positions. For example, as illustrated in FIG. 5B, in the position corresponding to the valve annulus 21 in the shape estimation model 200, the measuring function 555 calculates, "the maximum diameter ("Max Diameter"): 30.3 mm", "the minimum diameter ("Min Diameter"): 20.3 mm", "the perimeter: 80.3 mm", and "the area: 483.4 mm$^2$". The controlling function 551 causes the display 3 to display the calculated parameters.

Further, on the basis of the measured parameters, the controlling function 551 obtains conditions of the specification of an artificial valve being applicable, and further causes the display 3 to display the obtained conditions. For example, as illustrated in FIG. 5B, on the basis of the measured parameters, the controlling function 551 obtains, as a set of applicable conditions "Condition 1", "the diameter of the valve annulus ("Ann Diameter"): 18 mm-20 mm", "the diameter of the ascending aorta ("Aorta Diameter"): 20 mm-23 mm", "the diameter of the sinus of Valsalva ("SoV Diameter"): 25 mm-", "the height of the sinus of Valsalva ("SoV Height"): 15 mm-", and "the perimeter of the valve annulus ("Ann Perimeter"): 56.5 mm-62. 8 mm". Further, the controlling function 551 presents a comparative display of the obtained parameters with the measurement values.

In this situation, by applying a predetermined rule to the measurement values, the controlling function 551 is capable of obtaining the conditions of the specification of an artificial valve being applicable. For example, the memory 54 has stored therein, in advance, the rule to be applied to the measurement values. The controlling function 551 obtains the applicable conditions by reading the rule from the memory 54 and applying the rule to the measured parameter values.

As explained above, the controlling function 551 is configured to present the comparative display of the measurement values related to the shape of the heart valve with the applicable conditions of an artificial valve to be placed for the heart valve. As a result, the operator is able to determine, at a glance, the specification he/she should select and is thus able to easily determine the specification of the artificial valve to be placed.

As explained above, the ultrasound diagnosis apparatus 1 according to the first embodiment makes it possible to easily determine the specification of the artificial valve to be placed, by presenting the comparative display of the measurement values related to the shape of the heart valve, with the numerical values related to the shape of the artificial valve to be placed for the heart valve.

In this situation, the ultrasound diagnosis apparatus 1 is capable of further displaying various types of information. For example, the controlling function 551 is capable of causing an artificial valve model indicating an artificial valve designated by the operator and the shape estimation model to be displayed so as to be superimposed, in corresponding positions, over at least one selected from between a two-dimensional medical image and a three-dimensional medical image.

Figure 6:
FIG. 6 is a drawing illustrating yet another example of the display realized by the controlling function according to the first embodiment.

FIG. 6 is a drawing illustrating yet another example of the display realized by the controlling function 551 according to the first embodiment. Similarly to FIGS. 5A and 5B, FIG. 6 illustrates an example in which the controlling function 551 displays: the ultrasound images (the two images at the top and the one image at the bottom left) on the three cross-sectional planes taken of the valve annulus 21; a three-dimensional ultrasound image (one image at the bottom right) in which the images on the three cross-sectional planes are three-dimensionally arranged; and the measurement values of the shape estimation model ("Result" on the right side of the drawing).

For example, as illustrated in FIG. 6, the controlling function 551 causes an artificial valve model 300 indicating the shape of the artificial valve 30 to be displayed so as to be superimposed over the two-dimensional ultrasound images on the three cross-sectional planes and over the three-dimensional ultrasound image in which the two-dimensional ultrasound images are three-dimensionally arranged. In this situation, the artificial valve model 300 may be a model indicating the shape of the artificial valve selected by the operator or may be a model indicating the shape of an artificial valve satisfying the applicable conditions.

Further, in accordance with operations performed by the operator, the controlling function 551 is capable of changing the position in which the artificial valve model 300 is superimposed. In other words, via the input interface 4, the operator is able to arbitrarily change the position and the orientation of the artificial valve model 300 displayed over the ultrasound images. For example, to perform a simple surgery simulation, the operator is able to change the position and the orientation of the artificial valve model 300 having been selected. The controlling function 551 displays the artificial valve model 300 over the ultrasound images, so that the position and the orientation thereof change while following the changes made by the operator.

Further, the controlling function 551 is also capable of changing the display mode in accordance with the positional relationship between the artificial valve model and the shape estimation model. For example, the controlling function 551 is capable of displaying a contact region in an emphasized manner, in accordance with the degree by which the artificial valve model 300 and the shape estimation model 200 are in contact with each other. In one example, the controlling function 551 displays, in an emphasized manner, a contact region in which the degree of contact is high between the artificial valve model 300 and the shape estimation model 200 indicated with ellipses in the image at the top right of FIG. 6.

In this situation, the degree of contact between the artificial valve model 300 and the shape estimation model 200 may be expressed, for example, by indicating whether or not the artificial valve model 300 and the shape estimation model 200 are in contact with each other. In that situation, with respect to the artificial valve model 300 and the shape estimation model 200 displayed over the ultrasound image, the controlling function 551 displays the contact region in an emphasized manner, by changing the color of the contact region in which the two models are in contact with each other or by making the line bold in such a part of the curved line depicting the artificial valve model 300 where the two models are in contact with each other.

In another example, the degree of contact between the artificial valve model 300 and the shape estimation model 200 may be expressed, for example, by indicating a degree by which the artificial valve model 300 overlaps with the shape estimation model 200. In that situation, the controlling function 551 judges whether or not the display is to be emphasized, on the basis of how much the artificial valve model 300 spills over into the shape estimation model 200. In one example, when the contour line of the artificial valve model 300 spills over across the contour line of the shape estimation model 200, and the spill-over distance exceeds a distance corresponding to "5%" of the distance from the center of the shape estimation model 200 to the contour line, the controlling function 551 determines that the display is to be emphasized. When having determined that the display is to be emphasized, the controlling function 551 displays the spill-over region in an emphasized manner, by changing the color of the spill-over region or by making the line bold in such a part of the curved line depicting the artificial valve model 300 that corresponds to the spill-over.

The value "5%" used above is merely an example, and the percentage by which the display is determined to be emphasized may arbitrarily be set. Further, the percentage value does not need to be one, and two or more percentage values may be set. In that situation, the controlling function 551 exercises control so that the display is emphasized by using mutually-different modes for the mutually-different percentage values. For example, when the contour line of the artificial valve model 300 spills over across the contour line of the shape estimation model 200, the controlling function 551 presents the display while using mutually-different colors or mutually-different line thicknesses, for the region in which the spill-over distance exceeds the distance corresponding to "5%" of the distance from the center of the shape estimation model 200 to the contour line and for the region in which the spill-over distance exceeds a distance corresponding to "10%" of the same.

Further, the controlling function 551 is also capable of further causing measurement values to be displayed that are related to the shape of the heart valve measured on the basis of medical image data acquired by a medical image diagnosis apparatus of a type different from the type of the medical image diagnosis apparatus that acquired the medical image data. For example, the controlling function 551 further causes measurement values to be displayed that are related to the shape of the heart valve of the same subject and were measured on the basis of Computed Tomography (CT) image data or Magnetic Resonance Imaging (MRI) image data that is different from the ultrasound image data from which the shape estimation model was generated.

Figure 7:
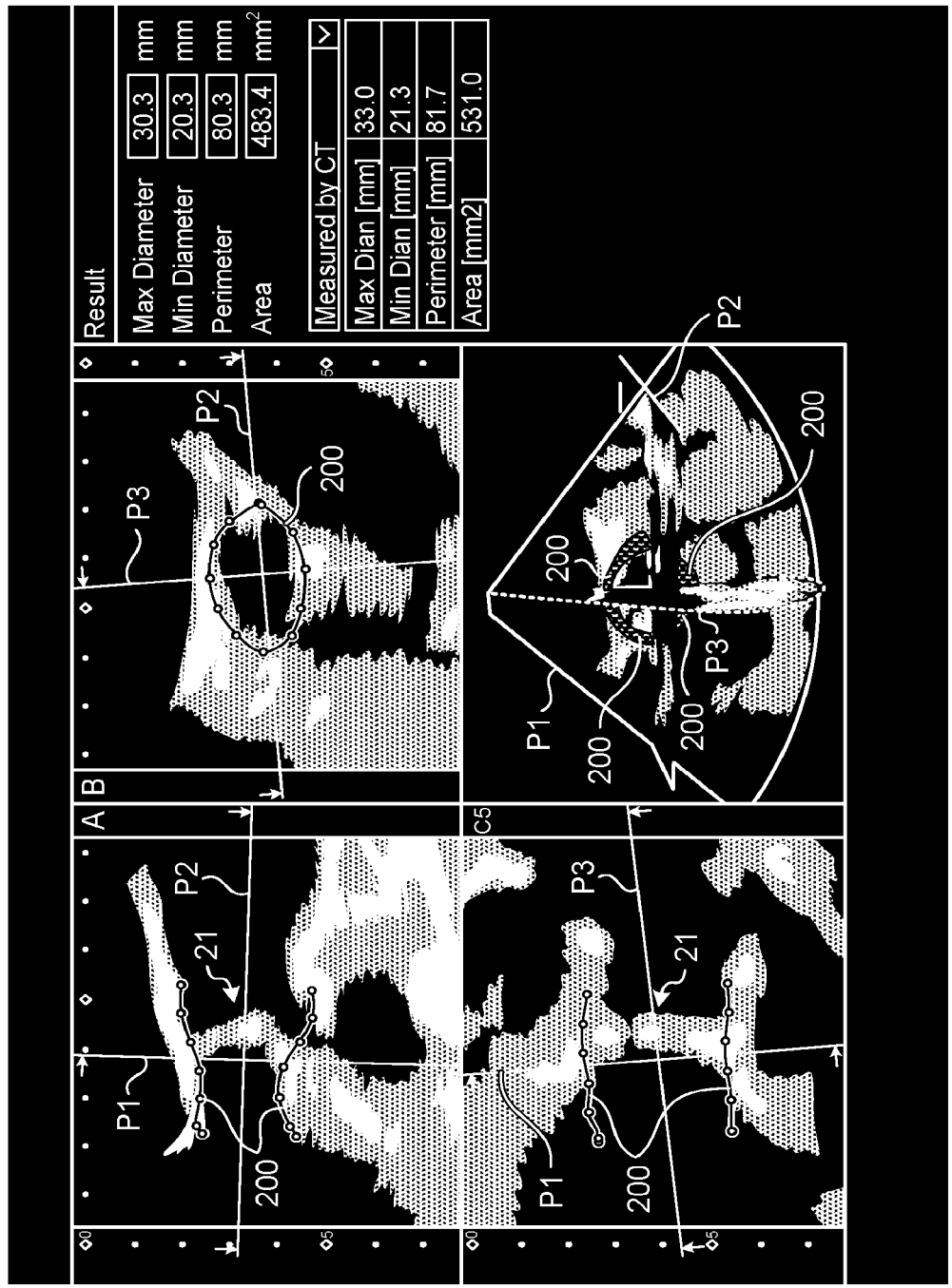
FIG. 7 is a drawing illustrating yet another example of the display realized by the controlling function according to the first embodiment.

FIG. 7 is a drawing illustrating yet another example of the display realized by the controlling function according to the first embodiment. Similarly to FIGS. 5A and 5B, FIG. 7 illustrates an example in which the controlling function 551 displays: the ultrasound images (the two images at the top and the one image at the bottom left) on the three cross-sectional planes taken of the valve annulus 21; the three-dimensional ultrasound image (the one image at the bottom right) in which the images on the three cross-sectional planes are three-dimensionally arranged; and the measurement values of the shape estimation model ("Result" on the right side of the drawing).

For example, as illustrated in FIG. 7, the controlling function 551 presents a comparative display of numerical values related to the shape of the aortic valve of the same subject measured by a CT apparatus, with the measurement values of the shape estimation model 200. In one example, the controlling function 551 displays values "Measured by CT" as: "the maximum diameter ("Max Dian"): 33.0 mm", "the minimum diameter ("Min Dian"): 21.3 mm", "the perimeter: 81.7 mm", and "the area: 531.0 mm$^2$".

In this situation, the controlling function 551 is capable of obtaining, in advance, the various types of parameters indicated as "Measured by CT", storing the obtained parameters into the memory 54, and displaying the parameters by reading the parameters from the memory 54. Alternatively, the controlling function 551 is also capable of obtaining CT image data at the time when the CT apparatus performs the measuring process, storing the CT image data into the memory 54, and further displaying parameter values from the CT image data corresponding to determined positions, when the operator has determined the positions in which the various types of parameters related to the shape of the shape estimation model 200 are to be measured.

In that situation, the controlling function 551 determines a positional correspondence relationship between the ultrasound image data and the CT image data, by performing a position alignment process between the CT image data stored in the memory 54 and the acquired ultrasound image data. On the basis of the determined correspondence relationship, the measuring function 555 extracts such a position in the CT image data that corresponds to the measurement position determined within the ultrasound image data and further performs a measuring process in the extracted position. For example, the measuring function 555 extracts such a position in the CT image data that corresponds to the position in which the "maximum diameter ("Max Diameter"): 30.3 mm" was measured and calculates the distance at the extracted position, as a "maximum diameter ("Max Dian"): 33.0 mm" within the CT image data.

The measuring process performed in the CT image data by the measuring function 555 may be performed so as to follow changes made to positions by the operator. In other words, while following the operations performed by the operator through the input interface 4, the measuring function 555 is capable of sequentially measuring parameters in various positions in the shape estimation model and parameters in such positions within the CT image data that correspond to the parameters in the various positions in the shape estimation model. Further, the controlling function 551 is capable of causing the parameters sequentially measured in the shape estimation model 200 and in the CT image data to be displayed, so as to sequentially change along with movements of the straight lines P1 to P3 defining the cross-sectional planes.

The parameters measured from the medical image data acquired by the other medical image diagnosis apparatus may be input through a manual input by the operator. Further, the controlling function 551 is also capable of causing a medical image to be displayed that is based on the medical image data acquired by the other medical image diagnosis apparatus. For example, the controlling function 551 is capable of causing the display screen illustrated in FIG. 7 to further display a CT image of the aortic valve generated on the basis of the CT image data.

Further, the controlling function 551 is also capable of further causing differences or errors to be displayed that are calculated between the parameters measured from the shape estimation model and the parameters measured from the medical image data acquired by the other medical image diagnosis apparatus. For example, the controlling function 551 is capable of calculating and displaying the difference "2.7 mm" between the "maximum diameter ("Max Diameter"): 30.3" of the valve annulus measured by using the shape estimation model 200 and the "maximum diameter ("Max Dian"): 33.0 mm" of the valve annulus measured by using the CT image data.

Further, the controlling function 551 is configured to further display one or more candidates for the artificial valve that are determined on the basis of the measurement values. More specifically, the controlling function 551 determines a suitable specification of the artificial valve on the basis of a relationship between the measurement values related to the shape of the shape estimation model and the applicable conditions of an artificial valve and further displays numerical values of the determined specification. In this situation, the controlling function 551 is capable of determining and displaying one or more suitable specifications of the artificial valve.

For example, the controlling function 551 extracts one specification of the artificial valve that best satisfies the applicable conditions with respect to the parameters and further displays the extracted specification of the artificial valve as a candidate (recommended) for the artificial valve to be placed. In this situation, the artificial valve that best satisfies the applicable conditions may denotes, for example, an artificial valve having the largest number of parameters satisfying the conditions or an artificial valve satisfying the condition of the parameter set with the highest degree of importance, after degrees of importance have been set with the parameters. For example, the degrees of importance are set so that, when there are two or more specifications that satisfy the same number of conditions, one of the specifications satisfying the condition regarding the diameter of the valve annulus is prioritized.

Figure 8:
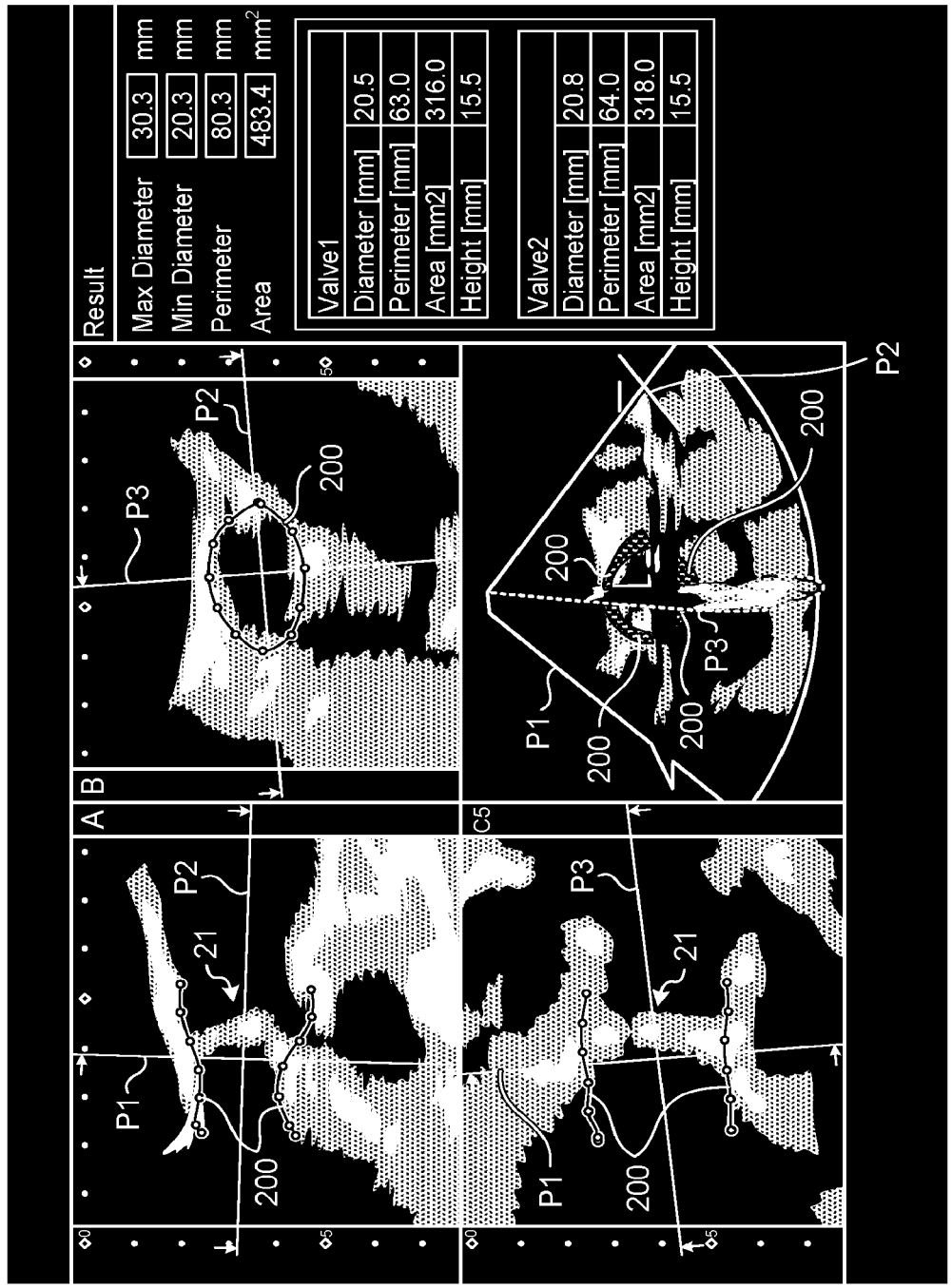
FIG. 8 is a drawing illustrating yet another example of the display realized by the controlling function according to the first embodiment.

Further, for example, the controlling function 551 is also capable of displaying a plurality of candidates for the artificial valve in descending order of priority levels. FIG. 8 is a drawing illustrating yet another example of the display realized by the controlling function according to the first embodiment. Similarly to FIGS. 5A and 5B, FIG. 8 illustrates an example in which the controlling function 551 displays: the ultrasound images (the two images at the top and the one image at the bottom left) on the three cross-sectional planes taken of the valve annulus 21; the three-dimensional ultrasound image (the one image at the bottom right) in which the images on the three cross-sectional planes are three-dimensionally arranged; and the measurement values of the shape estimation model ("Result" on the right side of the drawing).

For example, as illustrated in FIG. 8, on the basis of a relationship between the measurement values related to the shape of the shape estimation model and the applicable conditions of the artificial valve, the controlling function 551 extracts an artificial valve "Valve 1" having the highest priority level and another artificial "Valve 2" having the second highest priority level and displays the parameters of the extracted artificial valves in descending order of the priority levels. In this situation, for example, the priority levels indicate, for example, a descending order according to the number of parameters satisfying the conditions or a descending order according to the number of conditions satisfied with regard to one or more parameters having higher degrees of importance when degrees of importance have been set with the parameters. For example, the priority levels are set so that the more conditions are satisfied with regard to the diameter or the perimeter of the valve annulus, the higher is the priority level.

As explained above, the controlling function 551 is capable of displaying various types of information besides the comparative display of the measurement values related to the shape of the heart valve with the numerical values related to the shape of the artificial valve to be placed for the heart valve. In this situation, further, the controlling function 551 is also capable of displaying a correspondence relationship between parameter names or the measurement values thereof displayed on the screen and positions within the image. For example, when a cursor is placed on one of the parameter names or the measurement value thereof displayed on the screen, the controlling function 551 is capable of displaying, in an emphasized manner, the corresponding part within a two-dimensional ultrasound image or a three-dimensional ultrasound image.

In one example, the controlling function 551 displays the corresponding part in an emphasized manner by changing the color of the corresponding part, making the line of the corresponding part bold, displaying the corresponding part with two or more lines, or filling the corresponding part with solid color.

Figure 9:
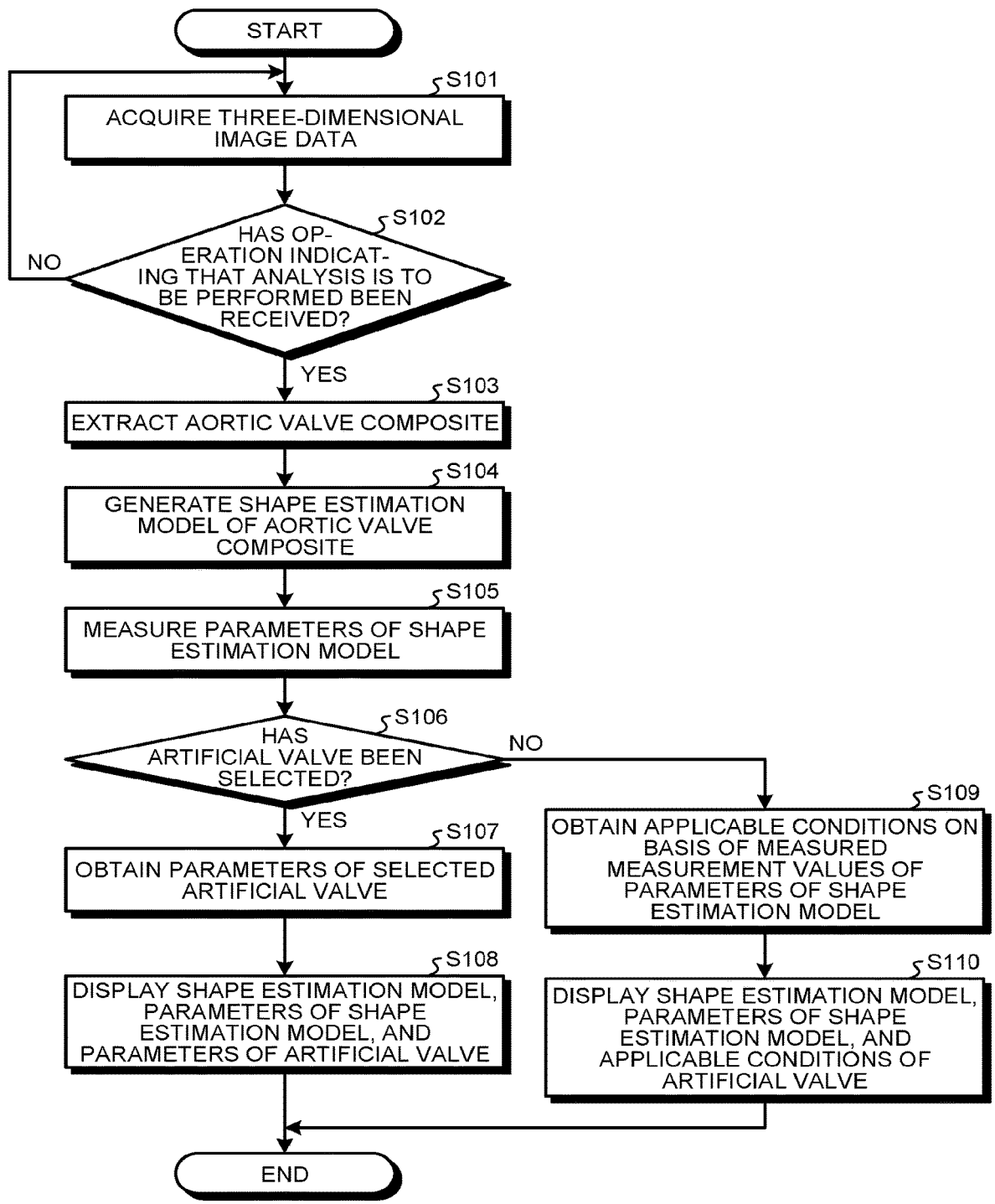
FIG. 9 is a flowchart for explaining procedures in processes performed by the ultrasound diagnosis apparatus according to the first embodiment.
Figure 10:
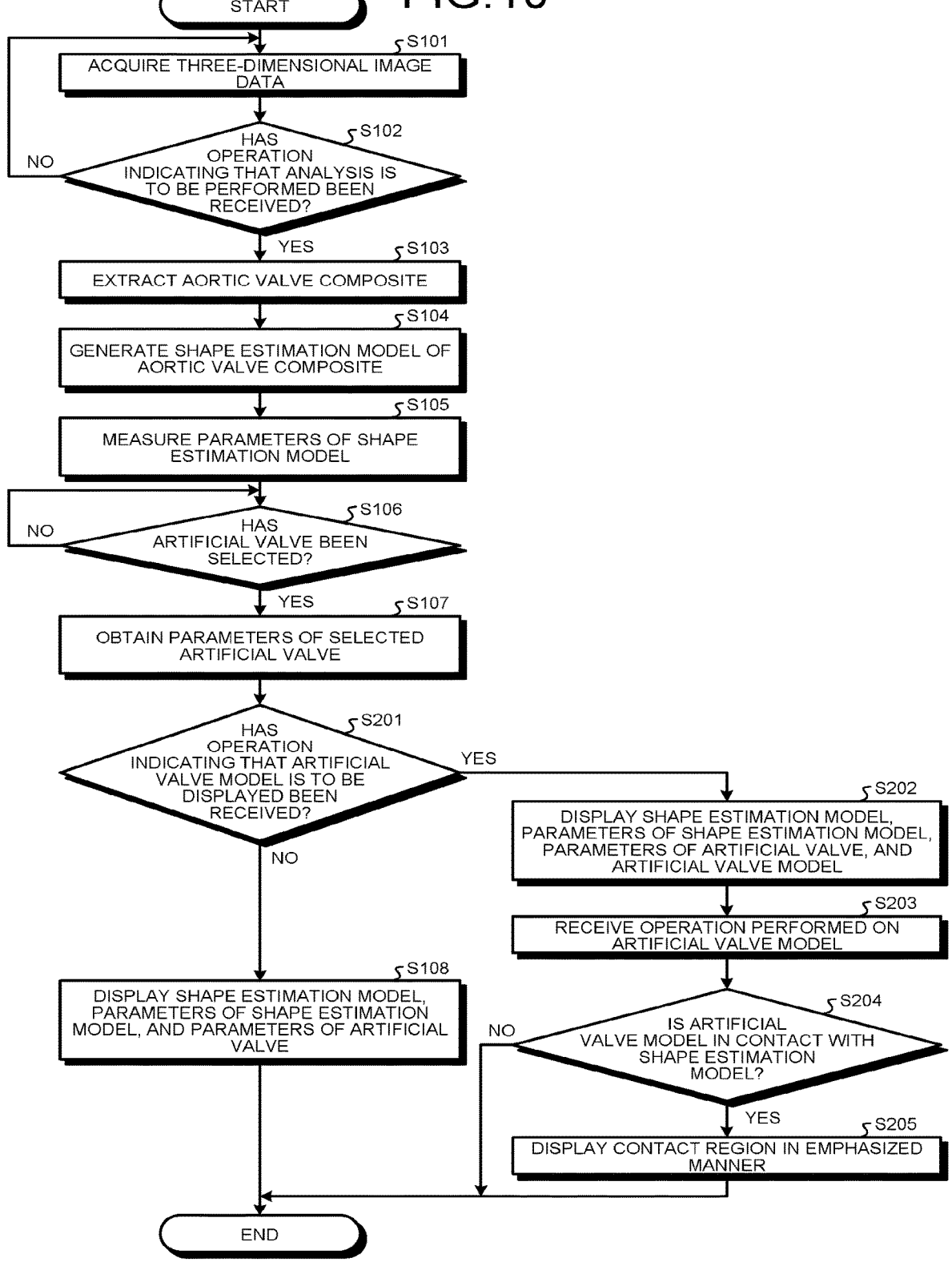
FIG. 10 is another flowchart for explaining the procedures in the processes performed by the ultrasound diagnosis apparatus according to the first embodiment.
Figure 11:
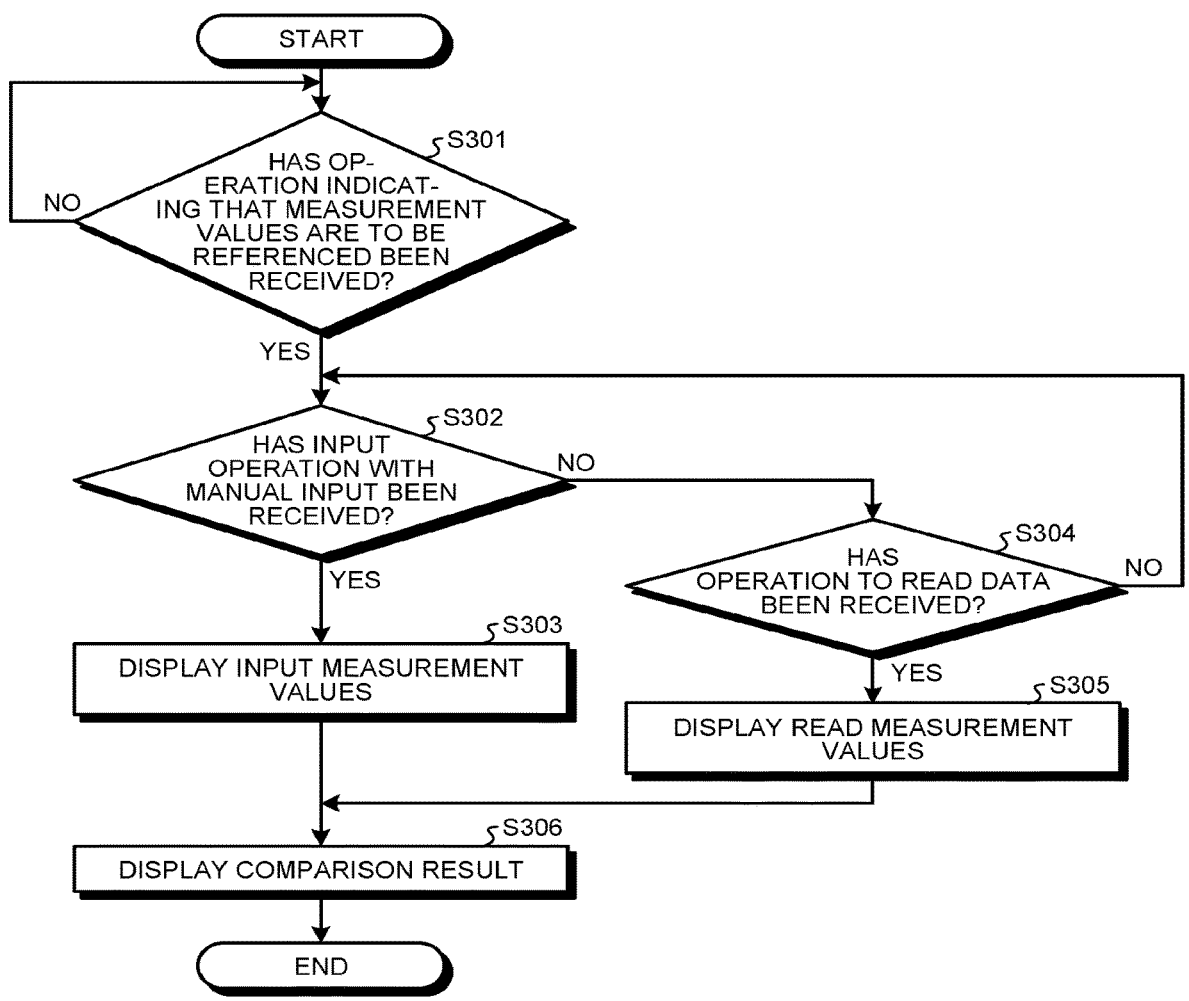
FIG. 11 is yet another flowchart for explaining the procedures in the processes performed by the ultrasound diagnosis apparatus according to the first embodiment.
Figure 12:
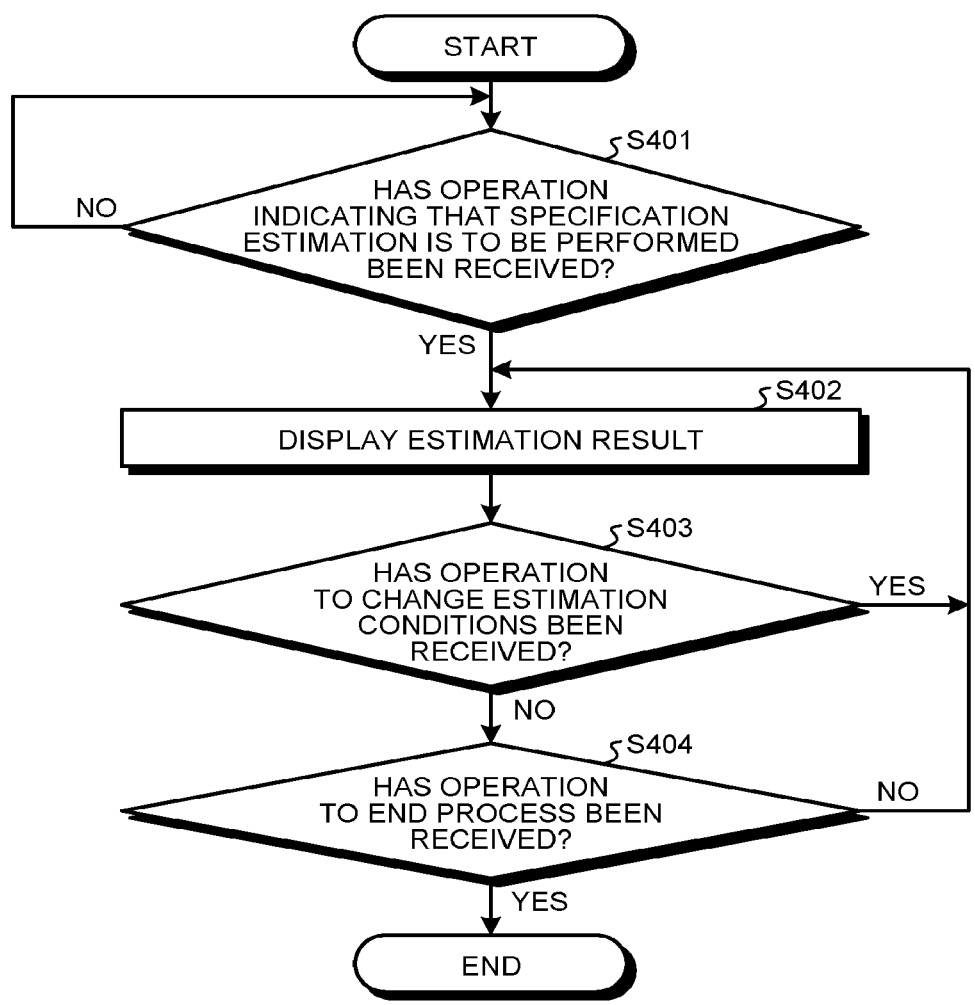
FIG. 12 is yet another flowchart for explaining the procedures in the processes performed by the ultrasound diagnosis apparatus according to the first embodiment.

Next, processes performed by the ultrasound diagnosis apparatus 1 according to the first embodiment will be explained, with reference to FIGS. 9 to 12. FIGS. 9 to 12 are flowcharts for explaining procedures in the processes performed by the ultrasound diagnosis apparatus 1 according to the first embodiment. FIG. 9 illustrates a process of displaying, as parameters indicating the shape of an artificial valve, numerical values indicating the shape of the artificial valve designated by the operator or conditions of the shape of an artificial valve applicable to the heart valve. FIG. 10 illustrates a process of displaying an artificial valve model. FIG. 11 illustrates a process of displaying measurement values based on medical image data obtained by another medical image diagnosis apparatus. FIG. 12 illustrates a process of displaying an artificial valve suitable for placement. Further, FIGS. 9 to 12 illustrate the processes using the aortic valve. FIGS. 11 and 12 illustrate the processes performed after measurement values of the shape estimation model are displayed.

Steps S101, S102, and S106 to S110 are steps at which the processing circuitry 55 reads and executes a program corresponding to the controlling function 551 from the memory 54. Step S103 is a step at which the processing circuitry 55 reads and executes a program corresponding to the extracting function 553 from the memory 54. Step S104 is a step at which the processing circuitry 55 reads and executes a program corresponding to the generating function 554 from the memory 54. Step S105 is a step at which the processing circuitry 55 reads and executes a program corresponding to the measuring function 555 from the memory 54.

Steps S201 through S205, S301 through S306, and S401 through S404 are steps at which the processing circuitry 55 reads and executes the program corresponding to the controlling function 551 from the memory 54.

As illustrated in FIG. 9, in the ultrasound diagnosis apparatus 1 according to the first embodiment, the processing circuitry 55 acquires three-dimensional image data (step S101), and judges whether or not an operation indicating that an analysis is to be performed has been received (step S102). In this situation, unless the operation is received (step S102: No), the ultrasound diagnosis apparatus 1 is in a standby state.

On the contrary, when the operation is received (step S102: Yes), the processing circuitry 55 extracts an aortic valve composite (step S103) and generates a shape estimation model of the aortic valve composite (step S104). Further, the processing circuitry 55 measures parameters of the shape estimation model (step S105) and judges whether or not an artificial valve has been selected (step S106).

When an artificial valve has been selected (step S106: Yes), the processing circuitry 55 obtains the parameters of the selected artificial valve (step S107) and displays the shape estimation model, the parameters of the shape estimation model, and the parameters of the selected artificial valve (step S108).

On the contrary, when no artificial valve has been selected (step S106: No), the processing circuitry 55 obtains applicable conditions on the basis of the measured measurement values of the parameters of the shape estimation model (step S109) and displays the shape estimation model, the parameters of the shape estimation model, and the applicable conditions of an artificial valve (step S110).

Further, in the ultrasound diagnosis apparatus 1 according to the first embodiment, as illustrated in FIG. 10, the processing circuitry 55 acquires three-dimensional image data (step S101) and judges whether or not an operation indicating that an analysis is to be performed has been received (step S102). In this situation, unless the operation is received (step S102: No), the ultrasound diagnosis apparatus 1 is in a standby state.

On the contrary, when the operation is received (step S102: Yes), the processing circuitry 55 extracts an aortic valve composite (step S103) and generates a shape estimation model of the aortic valve composite (step S104). Further, the processing circuitry 55 measures parameters of the shape estimation model (step S105) and judges whether or not an artificial valve has been selected (step S106). Unless the operation is received (step S106: No), the ultrasound diagnosis apparatus 1 is in a standby state.

On the contrary, when an artificial valve has been selected (step S106: Yes), the processing circuitry 55 obtains the parameters of the selected artificial valve (step S107) and judges whether or not an operation to have the artificial valve model displayed has been received (step S201). When the operation has not been received (step S201: No), the processing circuitry 55 displays the shape estimation model, the parameters of the shape estimation model, and the parameters of the selected artificial valve (step S108).

On the contrary, when the operation is received (step S201: Yes), the processing circuitry 55 displays the shape estimation model, the parameters of the shape estimation model, the parameters of the artificial valve, and the artificial valve model (step S202). Further, the processing circuitry 55 receives an operation performed on the artificial valve model (step S203) and judges whether or not the artificial valve model is in contact with the shape estimation model (step S204).

When the artificial valve model is in contact with the shape estimation model (step S204: Yes), the processing circuitry 55 displays the contact region in an emphasized manner (step S205). On the contrary, when the artificial valve model is not in contact with the shape estimation model (step S204: No), the processing circuitry 55 ends the process.

Further, in the ultrasound diagnosis apparatus 1 according to the first embodiment, as illustrated in FIG. 11, the processing circuitry 55 at first judges whether or not an operation indicating that the measurement values are to be referenced has been received (step S301). Unless the operation is received (step S301: No), the ultrasound diagnosis apparatus 1 is in a standby state.

On the contrary, when the operation is received (step S301: Yes), the processing circuitry 55 judges whether or not an input operation with a manual input has been received (step S302). When an input operation with a manual input is received (step S302: Yes), the processing circuitry 55 displays the input measurement values (step S303).

On the contrary, when no input operation with a manual input has been received (step S302: No), the processing circuitry 55 judges whether or not an operation to read data has been received (step S304). When no operation to read data has been received (step S304: No), the process returns to step S302 where the processing circuitry 55 judges whether or not an input operation with a manual input has been received. In other words, the processing circuitry 55 keeps performing the judging processes until an input operation with a manual input has been received or until an operation to read data has been received.

On the contrary, at step S304, when an operation to read data is received (step S304: Yes), the processing circuitry 55 displays the read measurement values (step S305). Further, after displaying the measurement values at step S303 or S305, the processing circuitry 55 displays a result of comparing the displayed measurement values with the measurement values of the shape estimation model (step S306).

Further, in the ultrasound diagnosis apparatus 1 according to the first embodiment, as illustrated in FIG. 12, the processing circuitry 55 at first judges whether or not an operation indicating that a specification estimation process is to be performed has been received (step S401). Unless the operation is received (step S401: No), the ultrasound diagnosis apparatus 1 is in a standby state.

On the contrary, when the operation is received (step S401: Yes), the processing circuitry 55 displays an estimation result (one or more candidates for the artificial valve) (step S402). Further, the processing circuitry 55 judges whether or not an operation to change the estimation conditions has been received (step S403).

In this situation, when an operation to change the estimation conditions is received (step S403: Yes), the process returns to step S402 where the processing circuitry 55 displays an estimation result (one or more candidates for the artificial valve) from the re-estimation. On the contrary, when no operation to change the estimation conditions has been received (step S403: No), the processing circuitry 55 judges whether or not an operation to end the process has been received (step S404). When an operation to end the process is received (step S404: Yes), the processing circuitry 55 ends the process. On the contrary, when no operation to end the process has been received (step S404: No), the processing circuitry 55 keeps displaying the estimation result.

As explained above, according to the first embodiment, the extracting function 553 is configured to extract the heart valve in the medical image data. The measuring function 555 is configured to measure the measurement values related to the shape of the extracted heart valve. The controlling function 551 is configured to present the comparative display of the measurement values with the numerical values related to the shape of the artificial valve to be placed for the heart valve. Accordingly, the ultrasound diagnosis apparatus 1 according to the first embodiment is capable of providing the comparative view of the measurement values related to the shape of the heart valve of the subject and the numerical values related to the shape of the artificial valve and thus makes it possible to facilitate the process of determining the specification of the artificial valve to be placed.

Further, according to the first embodiment, the controlling function 551 is configured to present the comparative display of the measurement values with one selected from between: the numerical values indicating the shape of the artificial valve designated by the operator; and the conditions of the shape of an artificial valve applicable to the heart valve. Consequently, the ultrasound diagnosis apparatus 1 according to the first embodiment is able to display the information used for determining the specification of the artificial valve and thus makes it possible to facilitate the process of determining the specification of the artificial valve to be placed.

Further, according to the first embodiment, the generating function 554 is configured to generate the heart valve model (the shape estimation model) indicating the shape of the heart valve extracted by the extracting function 553. The measuring function 555 is configured to measure the measurement values related to the shape of the heart valve model (the shape estimation model). Consequently, the ultrasound diagnosis apparatus 1 according to the first embodiment makes it possible to easily measure the various types of parameters related to the shape of the heart valve.

Further, according to the first embodiment, the controlling function 551 is configured to cause the artificial valve model indicating the artificial valve designated by the operator and the heart valve model to be displayed so as to be superimposed, in the corresponding position, over at least one selected from between a two-dimensional medical image and a three-dimensional medical image. Consequently, the ultrasound diagnosis apparatus 1 according to the first embodiment is able to facilitate the process of comparing the heart valve model (the shape estimation model) with the artificial valve model and thus makes it possible to facilitate the process of determining the specification of the artificial valve to be placed.

Further, according to the first embodiment, the controlling function 551 is configured to further cause the measurement values to be displayed that are related to the shape of the heart valve measured on the basis of the medical image data acquired by the medical image diagnosis apparatus of a type different from the type of the medical image diagnosis apparatus that acquired the medical image data. Consequently, the ultrasound diagnosis apparatus 1 according to the first embodiment enables the comparison using the measurement values based on the other data and thus makes it possible to further facilitate the process of determining the specification of the artificial valve to be placed.

Further, according to the first embodiment, the controlling function 551 is configured to cause the medical image to be displayed that is based on the medical image data acquired by the medical image diagnosis apparatus of the different type. Consequently, the ultrasound diagnosis apparatus 1 according to the first embodiment enables the comparison using the image based on the other data and thus makes it possible to further facilitate the process of determining the specification of the artificial valve to be placed.

Further, according to the first embodiment, the controlling function 551 is configured to further display the one or more candidates for the artificial valve determined based on the measurement values. Consequently, the ultrasound diagnosis apparatus 1 according to the first embodiment makes it possible to further display the information that assists the process of determining the specification of the artificial valve to be placed.

Further, according to the first embodiment, the controlling function 551 is configured to display the plurality of candidates for the artificial valve in the descending order of the priority levels. Consequently, the ultrasound diagnosis apparatus 1 according to the first embodiment makes it possible to facilitate the judgment in determining the specification of the artificial valve to be placed.

Other Embodiments

The first embodiment has thus been explained. It is however, possible to carry out the present disclosure in various different modes other than those described in the first embodiment.

In the first embodiment above, the example using the aortic valve is explained; however, possible embodiments are not limited to this example. For instance, other heart valves such as the mitral valve or the tricuspid valve may be used.

Further, in the embodiments described above, the example is explained in which the shape estimation model is generated so as to measure the various types of parameters by using the generated shape estimation model; however, possible embodiments are not limited to this example. For instance, it is also acceptable to measure the various types of parameters by using three-dimensional medical image data, without generating the shape estimation model.

Further, in the embodiments described above, the example is explained in which the medical image processing apparatus of the present disclosure is incorporated in the ultrasound diagnosis apparatus 1, so that the ultrasound diagnosis apparatus 1 performs the various types of processes; however, possible embodiments are not limited to this example. It is also acceptable to have the medical image processing apparatus of the present disclosure incorporated in a medical image diagnosis apparatus of a different type such as an X-ray CT apparatus, an MRI apparatus or the like. In that situation, the medical image processing apparatus is configured to perform the processes described above, by using medical image data acquired by the incorporating medical image diagnosis apparatus.

Further, in the embodiments described above, the example is explained in which the CT image data is used as the medical image data acquired by the other medical image diagnosis apparatus; however, possible embodiments are not limited to this example. For instance, MRI image data may be used. In other words, the combination of the medical image data may be an arbitrary combination.

Further, in the embodiments described above, the example is explained in which the three cross-sectional planes orthogonal to the valve annulus 21 are set (see FIG. 5A, for example); however, possible embodiments are not limited to this example. It is possible to arbitrarily set cross-sectional planes with respect to the valve annulus 21. For example, a cross-sectional plane (e.g., the plane P1 in FIG. 5A) going through the base of a cusp of the aortic valve and another cross-sectional plane (e.g., the plane P2 in FIG. 5A) positioned along the blood flow direction do not necessarily have to be orthogonal to each other. Even in that situation, the medical image processing apparatus of the present disclosure is able to set the cross-sectional planes that are not orthogonal to each other.

Further, in the embodiments described above, the example is explained in which the medical image processing apparatus of the present disclosure is incorporated in the medical image diagnosis apparatus; however, possible embodiments are not limited to this example. The medical image processing apparatus alone may perform the processes. In that situation, the medical image processing apparatus includes: processing circuitry configured to perform the same processes as those performed by the controlling function 551, the extracting function 553, the generating function 554, and the measuring function 555 described above; and a memory configured to store therein the programs corresponding to the functions and the information related to the artificial valves. Further, the processing circuitry is configured to obtain the three-dimensional medical image data from a medical image diagnosis apparatus such as an ultrasound diagnosis apparatus or an image storage device via a network and to perform the processes described above by using the obtained medical image data. In this situation, the processing circuitry is a processor configured to realize the functions corresponding to the programs, by reading and executing the programs from the memory.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions by reading and executing the programs saved in a memory. In this situation, instead of saving the programs in the memory, it is also acceptable to directly incorporate the programs in the circuits of the processors. In that situation, the processors realize the functions by reading and executing the programs incorporated in the circuits thereof. The processors in the present embodiments do not each necessarily have to be structured as a single circuit. It is also acceptable to structure one processor by combining together a plurality of independent circuits so as to realize the functions thereof.

Further, the constituent elements of the apparatuses and the devices illustrated in the drawings referenced in the description of the above embodiments are based on functional concepts. Thus, it is not necessary to physically configure the constituent elements as indicated in the drawings. In other words, specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program analyzed and executed by the CPU or may be realized as hardware using wired logic.

Further, it is possible to realize the processing methods described in any of the embodiments above by causing a computer such as a personal computer or a workstation to execute a processing program prepared in advance. It is possible to distribute the processing program via a network such as the Internet. Further, it is also possible to record the processing program onto a computer-readable non-transitory recording medium such as a hard disk, a flexible disk (FD), a Compact Disk Read-Only Memory (CD-ROM), a Magneto Optical (MO) disk, a Digital Versatile Disk (DVD), a flash memory such as a Universal Serial Bus (USB) memory or a Secure Digital (SD) card memory, or the like, so as to be executed as being read from the non-transitory recording medium by a computer.

As explained above, according to at least one aspect of the embodiments, it is possible to facilitate the process of determining the specification of the artificial valve to be placed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry configured to
obtain medical image data including a heart valve of a subject;
generate a heart valve model that estimates a shape of the heart valve of the subject using the medical image data;
measure a measurement value related to the shape of the heart valve of the subject using the heart valve model; and
cause a display to display the measurement value and a numerical value related to a shape of an artificial valve to be placed for the heart valve of the subject.

2. The medical image processing apparatus according to claim 1, wherein the processing circuitry is configured to cause the display to display the numerical value related to the shape of the artificial valve to be placed for the heart valve of the subject, together with the measurement value.

3. The medical image processing apparatus according to claim 2, wherein the processing circuitry is configured to cause the display to display the measurement value and the numerical value related to the shape of the artificial valve to be placed for the heart valve of the subject, so as to be arranged side by side.

4. The medical image processing apparatus according to claim 1, wherein, as the numerical value related to the shape of the artificial valve to be placed for the heart valve of the subject, the processing circuitry is configured to cause the display to display, together with the measurement value, one selected from between: the numerical value indicating the shape of the artificial valve designated by an operator; and the numerical value indicating a condition of the shape of the artificial valve applicable to the heart valve of the subject.

5. The medical image processing apparatus according to claim 1, wherein the processing circuitry is configured to cause the display to display an artificial valve model indicating the artificial valve designated by an operator and the heart valve model so as to be superimposed, in a corresponding position, over a two-dimensional medical image.

6. The medical image processing apparatus according to claim 5, wherein the processing circuitry is configured to change a display mode of one selected from between the artificial valve model and the heart valve model, in accordance with a positional relationship between the artificial valve model and the heart valve model.

7. The medical image processing apparatus according to claim 1, wherein the processing circuitry is configured to cause the display to further display a measurement value related to the shape of the heart valve measured on a basis of medical image data acquired by a medical image diagnosis apparatus of a type different from a type of a medical image diagnosis apparatus that acquired the medical image data.

8. The medical image processing apparatus according to claim 7, wherein the processing circuitry is configured to cause the display to further display a medical image based on the medical image data acquired by the medical image diagnosis apparatus of the different type.

9. The medical image processing apparatus according to claim 1, wherein the processing circuitry is configured to cause the display to further display one or more candidates for the artificial valve determined on a basis of the measurement value.

10. The medical image processing apparatus according to claim 9, wherein the processing circuitry is configured to cause the display to display a plurality of candidates for the artificial valve in descending order of priority levels.

11. The medical image processing apparatus according to claim 1, wherein the medical image data is ultrasound image data.

12. The medical image processing apparatus according to claim 1, wherein the processing circuitry is configured to cause the display to display an artificial valve model indicating the artificial valve designated by an operator and the heart valve model so as to be superimposed, in a corresponding position, over a three-dimensional medical image.

13. The medical image processing apparatus according to claim 12, wherein the processing circuitry is configured to change a display mode of one selected from between the artificial valve model and the heart valve model, in accordance with a positional relationship between the artificial valve model and the heart valve model.

14. A medical image processing method comprising:
obtaining medical image data including a heart valve of a subject;
generating a heart valve model that estimates a shape of the heart valve of the subject using the medical image data;
measuring a measurement value related to the shape of the heart valve of the subject using the heart valve model; and
causing a display to display the measurement value and a numerical value related to a shape of an artificial valve to be placed for the heart valve of the subject.

15. A storage medium storing therein, in a non-transitory manner, a program configured to cause a computer to execute:
an obtaining step of obtaining medical image data including a heart valve of a subject;
a generating step of generating a heart valve model that estimates a shape of the heart valve of the subject using the medical image data;
a measuring step of obtaining a measurement value related to the shape of the heart valve of the subject using the heart valve model; and
a controlling step of causing a display to display the measurement value and a numerical value related to a shape of an artificial valve to be placed for the heart valve of the subject.

* * * * *